United States Patent
Dreyer et al.

(10) Patent No.: US 8,199,326 B2
(45) Date of Patent: Jun. 12, 2012

(54) GAS CONCENTRATION-MEASURING DEVICE

(75) Inventors: Peter Dreyer, Pansdorf (DE); Günter Steinert, Bad Oldesloe (DE); Alfred Kelm, Badendorf (DE); Christian Jäger, Lübeck (DE); Livio Fornasiero, Bliestorf (DE); Hartmut Stark, Stockelsdorf (DE); Ralf Buchtal, Lübeck (DE); Burkhard Stock, Lübeck (DE); Ralf Döring, Lübeck (DE); Anja Künzel, legal representative, Lübeck (DE)

(73) Assignee: Drägerwerk AG & Co., KGaA, Lübeck (DE)

( * ) Notice: Subject to any disclaimer, the term of this patent is extended or adjusted under 35 U.S.C. 154(b) by 332 days.

(21) Appl. No.: 12/689,525

(22) Filed: Jan. 19, 2010

(65) Prior Publication Data
US 2010/0225917 A1    Sep. 9, 2010

(30) Foreign Application Priority Data
Mar. 3, 2009    (DE) .......................... 10 2009 011 421

(51) Int. Cl.
*G01B 9/02* (2006.01)
*G01N 21/00* (2006.01)

(52) U.S. Cl. ........................ 356/454; 356/437; 356/519

(58) Field of Classification Search ................... 356/454, 356/480, 506, 519
See application file for complete search history.

(56) References Cited

U.S. PATENT DOCUMENTS

| | | | |
|---|---|---|---|
| 3,915,573 A * | 10/1975 | Knoll et al. ................... | 356/454 |
| 5,218,422 A | 6/1993 | Zoechbauer | |
| 5,300,778 A | 4/1994 | Norkus et al. | |
| 5,477,051 A | 12/1995 | Tsuchiya | |
| 5,739,535 A | 4/1998 | Koch et al. | |
| 5,835,216 A | 11/1998 | Koskinen | |
| 5,920,391 A | 7/1999 | Grasdepot et al. | |
| 7,359,066 B2 * | 4/2008 | Cummings et al. ........... | 356/519 |
| 2001/0015810 A1 | 8/2001 | Hara et al. | |
| 2008/0074647 A1 | 3/2008 | Doring et al. | |

FOREIGN PATENT DOCUMENTS

| | | |
|---|---|---|
| DE | 39 25 692 C1 | 8/1990 |
| DE | 196 28 310 C2 | 5/1998 |
| DE | 102 26 305 C1 | 10/2003 |
| DE | 102006045253 | 12/2007 |
| EP | 0 536 727 B1 | 4/1993 |
| GB | WO 2005/054827 | 6/2005 |

* cited by examiner

*Primary Examiner* — Hwa Lee
(74) *Attorney, Agent, or Firm* — McGlew and Tuttle, P.C.

(57) ABSTRACT

A gas concentration-measuring device makes it possible to measure gas components in a gas sample. An interferometer, based on a dual-band Fabry-Perot interferometer (1), is provided with a transmission spectrum that can be set by a control voltage (38). The control voltage (38) of the dual-band Fabry-Perot interferometer (1) is synchronized over the course of time with the activation and deactivation of the radiation sources (11, 12).

31 Claims, 13 Drawing Sheets

GAS CONCENTRATION-MEASURING DEVICE

CROSS REFERENCE TO RELATED APPLICATIONS

This application claims the benefit of priority under 35 U.S.C. §119 of German Patent Application DE 10 2009 011 421.1 filed Mar. 3, 2009, the entire contents of which are incorporated herein by reference.

FIELD OF THE INVENTION

The present invention pertains to a process for operating a gas concentration-measuring device for determining the percentages of inhalation anesthetics, carbon dioxide, laughing gas and alcohol compounds in a gas sample and to a device for carrying out the process.

BACKGROUND OF THE INVENTION

Infrared optical systems with optical interference filters are frequently used to measure the gas concentrations of anesthetic gases such as inhalation anesthetics, carbon dioxide and laughing gas and also to determine the alcohol concentration in the breathing air of a person.

A gas analyzer known from DE 196 28 310 C2 comprises a radiation source, a measuring path receiving the gas sample and a detector, which is connected to an analyzing circuit. Different interference filters are brought one after another into the ray path by means of a rotating filter wheel. The transmission wavelengths of the filters are coordinated in the technical embodiment of the measuring arrangement with the absorption wavelengths of the gas components to be determined. To measure inhalation anesthetics, the transmission wavelengths of the filters are in a range of 8 µm to 12 µm, whereas those for laughing gas and carbon dioxide are in a range of 4 µm to 6 µm. The filter and transmission wavelength needed to measure drinkable alcohols is at 9.46 µm. Filters with a transmission wavelength of 3.4 µm and with a transmission wavelength range from 8.2 µm to 9.8 µm are advantageous for the measurement of acetone. Filters with a transmission wavelength range from 8.2 µm to 9.8 µm are likewise advantageous for the measurement of essential oils. Alcohol compounds and essential oils, for example, peppermint oil, can also be distinguished from each other besides the possibility to distinguish inhalation anesthetics from laughing gas and carbon dioxide. This makes it possible in case of patients whose alcohol concentration in the expired air is unphysiologically elevated to minimize the effect on the measuring results, which is associated therewith, in the determination of the gas concentration values of anesthetics and laughing gas.

The checking of the fitness of vehicle drivers to drive in connection with the monitoring of road traffic by measuring the breath alcohol concentration arises as an additional application from the possibility of distinguishing alcohols from essential oils. DE 10 2006 045 253 B3 describes a gas concentration-measuring device in which the absorption wavelengths are tuned with a dual-band Fabry-Perot interferometer. This has the advantage that the mechanically sensitive rotating filter wheel may be dispensed with in the arrangement and the device therefore has a more robust design against mechanical stresses. Another advantage is that the dual-band Fabry-Perot interferometer lets the wavelengths pass through in two spectral ranges. The transmission band of the dual-band Fabry-Perot interferometer is changed in this case by means of a control voltage such that both wavelength ranges are detected with one detector element and both wavelength ranges are analyzed simultaneously. To tune the wavelength ranges, the control voltage is applied electrically to the dual-band Fabry-Perot interferometer as a ramp function rising from a starting value to an end value and finally dropping again to the starting value. Two radiation sources, one source in the range of 4 µm to 6 µm, and another source in the range from 8 µm to 12 µm, are used as light sources. A broad-band radiation source, which emits light in the wavelength range from 4 µm to 12 µm, may be used as an alternative. By means of modulated radiation sources and a lock-in method, the dual-band Fabry-Perot interferometer is used in such an arrangement to simultaneously detect both wavelength ranges, to separate the measured values of the two wavelength ranges from one another and to analyze them. FIG. 1 of DE 10 2006 045 253 B3 shows the schematic diagram of a dual-band Fabry-Perot interferometer. A device for measuring gases, comprising a Fabry-Perot interferometer and a detector, is shown in US 2001015810A. A detector for detecting a plurality of spectral ranges is shown in EP 0536727 B1 in an embodiment as a multispectral sensor. The multispectral sensor comprises an array of optical elements for beam splitting in the form of a pyramid, whose reflection and transmission properties are spectrally different. The light is thus spectrally deflected selectively to the corresponding radiation-sensitive elements. A Fabry-Perot interferometer driven electrostatically, by means of a control voltage, is shown in DE 10226305 C1.

In terms of its transmission characteristic, the dual-band Fabry-Perot interferometer possesses the disadvantageous property of hysteresis of the transmitted wavelength when the control voltage is raised and lowered. This causes the association between the control voltage and the transmission wavelength to be different for the rising ramp of the control voltage and for the sloping ramp of the control voltage. Therefore, either only the rising part or the dropping part of the control voltage can be used for the analysis. An effective rate of measurement of 1 Hz is necessary for the application in the measurement of anesthetic gases and breath alcohol for a measurement resolution for each breath in inspiration and expiration. A repetition frequency of 2 Hz is necessary for this for running through a complete ramp of the control voltage for tuning two wavelength ranges of the dual-band Fabry-Perot interferometer when analyzing only one ramp of the control voltage. Modulation of the radiation source is necessary for the application of the lock-in method. To obtain sufficient spectral information in the received signal, a modulation frequency that is higher by a factor of at least 10 than the repetition frequency for tuning the dual-band Fabry-Perot interferometer is necessary for a robust technical embodiment. A distance of the modulation frequency by a factor of 3 is necessary in the practical and measuring technical embodiment for distinguishing two spectral ranges of interest from the spectral information for the two spectral ranges. This means, as a result, that a modulation frequency of 20 Hz is necessary for the first wavelength range of interest and a modulation frequency of 60 Hz is necessary for the second wavelength range of interest. When using a thermal radiation source, there is a significant decrease in amplitude with increasing modulation frequency above a modulation frequency of 30 Hz as a property of the thermal radiation source, which adversely affects the signal-to-noise ratio of the received signal, so that the signal is hidden by the noise level for the second wavelength range of interest and it can no longer be detected. This means that a value of 30 Hz is used as the highest modulation frequency for the second wavelength range of interest, which then leads, in conclusion, to a modulation frequency of 10 Hz for the first wavelength range of interest and results in a value of 0.5 Hz for the rate of measurement. Thus, the breathing gas concentration is not determined with a time resolution that would make it possible to distinguish the concentration values for inspiration and expiration.

SUMMARY OF THE INVENTION

The basic object of the present invention is to propose a gas concentration-measuring device and a process for operating a gas concentration-measuring device, with which the measurement of breathing gases can be resolved for individual phases of breathing.

According to the invention, a process for operating a gas concentration-measuring unit is provided. The process comprises providing the gas concentration-measuring unit with a dual-band Fabry-Perot interferometer, with a first infrared radiation source for a first wavelength range from 4 µm to 6 µm and with a second infrared radiation source for a second wavelength range from 8 µm to 12 µm, switching the infrared radiation sources on and off by means of light control signals, tuning the dual-band Fabry-Perot interferometer over a wavelength range by means of a control voltage and synchronizing the control voltage with the light control signals.

According to another aspect of the invention, a process is provided for operating a dual-band Fabry-Perot interferometer with a first infrared radiation source and a second infrared radiation source. The infrared radiation sources are switched on and off by means of light control signals. The dual-band Fabry-Perot interferometer is tuned over a wavelength by means of a variable ramp function control voltage having a first ramp and a second ramp. The first ramp of the control voltage is delayed relative to a first light switching signal of a first radiation source by a delay time. The second ramp of the control voltage is delayed relative to a second light switching signal of the second radiation source by another delay time. The delay time and the another delay time correspond to the respective time constants of the first and second radiation sources.

The delay time may correspond to a fall time of the second radiation source and the build-up time of the first radiation source. The another delay time may correspond to a fall time of the first radiation source and a build-up time of the second radiation source.

According to another aspect of the invention, a process is provided for operating a dual-band Fabry-Perot interferometer with a first infrared radiation source and a second infrared radiation source including checking the dual-band Fabry-Perot interferometer. The infrared radiation sources are switched on and off by means of light control signals. The dual-band Fabry-Perot interferometer is tuned over a wavelength by means of a variable ramp function control voltage having a first ramp and a second ramp. The first ramp of the control voltage is delayed relative to a first light switching signal of a first radiation source by a delay time. The second ramp of the control voltage is delayed relative to a second light switching signal of the second radiation source by another delay time. The delay time and the another delay time correspond to the respective time constants of the first and second radiation sources. The delay time may be the sum of a build-up time of the first radiation source, a measuring time and a fall time of the second radiation source and the another delay time may be the sum of a build-up time of the second radiation source, a measuring time and a fall time of the first radiation source.

A process is further provided including detecting and monitoring, with the gas concentration-measuring unit, the gas concentration of laughing gas, carbon dioxide, inhalation anesthetics and alcohols in the breathing gas of a person and/or breathing circuit of an anesthesia apparatus. A process is further provided including detecting and monitoring, with the gas concentration-measuring unit, the gas concentration of alcohols in the breathing gas of a person in the determination of the fitness to drive in road traffic or in alcohol concentration measurement for determining the fitness to work in business with respect to work activities that may be hazardous.

According to another aspect of the invention, a device is provided for gas concentration measurement. The device comprises a dual-band Fabry-Perot interferometer; a first infrared radiation source for providing radiation of a first wavelength range from 4 µm to 6 µm, a second infrared radiation source for providing a second wavelength range from 8 µm to 12 µm and an actuating means for changing a direction of tuning of the dual-band Fabry-Perot interferometer. A switching means is provided for mutually switching the infrared radiation sources on and off at the time of a change in the spectral transmission band of the dual-band Fabry-Perot interferometer.

According to another aspect of the invention, a device is provided for gas concentration measurement. The device comprises a dual-band Fabry-Perot interferometer, a first infrared radiation source providing radiation of a first wavelength range from 4 µm to 6 µm, a second infrared radiation source providing radiation of a second wavelength range from 8 µm to 12 µm and an actuating means for changing a direction of tuning of the dual-band Fabry-Perot interferometer. A switching means is provided for mutually switching the infrared radiation sources on and off at the time of a change in the direction of tuning of the dual-band Fabry-Perot interferometer.

The advantage of the present invention is essentially that two band-limited radiation sources are combined with one another in an arrangement in connection with a dual-band Fabry-Perot interferometer and the actuating signals for tuning the transmission in the spectral range of the dual-band Fabry-Perot interferometer are synchronized with the two radiation sources. The two radiation sources are tuned in the radiated wavelength to the wavelength ranges and the transmissions of a first transmission band and of a second transmission band in the spectrum of the dual-band Fabry-Perot interferometer. The light radiated by the radiation sources passes through a measuring path, in which the gas sample to be analyzed is contained and reaches the dual-band Fabry-Perot interferometer at the end of the measuring path. After passing through the dual-band Fabry-Perot interferometer, the light radiated by the radiation source falls on at least one first detector. Detectors for detecting the infrared light are known from WO 2005054827, where, for example, detectors with the type designations LIM122 (InfraTec) or LHi814 (Perkin Elmer) are mentioned. The at least first detector is designed to selectively detect the light of the first spectral transmission band, and a second detector is designed to detect the light of the second transmission band. The first and second detectors may also be combined in one structural unit as a dual-band detector. A sensor arranged in a structural unit for detecting a plurality of spectral ranges is described in EP 0536727 B1. The spectral detection ranges of the detectors are preferably tuned to the transmissions of the first and second transmission bands of the dual-band Fabry-Perot interferometer.

The dual-band Fabry-Perot interferometer is advantageously tuned by means of a ramp-like control voltage over the wavelength range of interest. In another preferred manner, the ramp-like control voltage is linear and the transmission wavelength is tuned variably uniformly over the wavelength range. In yet another preferred manner, the ramp-like control voltage is nonlinear. The nonlinearity of the control voltage is such that it is nonlinear over the entire course or is nonlinear in some sections. The nonlinearity is selected to be such that nonlinear properties of the transfer function of the dual-band Fabry-Perot interferometer are compensated. If the transfer function of the dual-band Fabry-Perot interferometer has, for example, a partially square course, this effect can be compensated by a control voltage that consists of a function with a square root component. The course of the control voltage may be stored in the measuring device both by mathematical equations and in a tabular form.

Due to the actuation of the dual-band Fabry-Perot interferometer with the control voltage, the transmission of said dual-band Fabry-Perot interferometer is passed through in a first wavelength range of $\Delta\lambda_1 = 4$ µm to 6 µm in the first transmission band and in a second transmission band of $\Delta\lambda_2 = 8$ µm to 12 µm.

The spectral range defined by the indicated limits of the two wavelength ranges comprises essentially the measuring ranges for the gases carbon dioxide, laughing gas, volatile anesthetics as well as alcohols, which are relevant for gas measurement in the expired air and can be measured by means of infrared absorption. With the indicated wavelength ranges from 4 µm to 6 µm and 8 µm to 12 µm, wavelengths that are spectrally close above and below these indicated limits are also covered in the sense of the present invention; acetone, with an absorption wavelength of 3.36 µm, shall be mentioned here as an example.

Table 1 below shows a review of substances encountered in medical engineering, of metabolites of the human body and of measurable drinkable alcohols, as well as of some essential oils, which are measurable in the area of the two wavelength ranges by means of infrared absorption, with an association with the two wavelength ranges $\Delta\lambda_1$ and $\Delta\lambda_2$.

| Measurable substances | First wavelength range $\Delta\lambda_1 = 4$ µm to 6 µm (data in µm) | Second wavelength range $\Delta\lambda_2 = 8$ µm to 12 µm (date in µm) |
| --- | --- | --- |
| Medical gases | | |
| Laughing gas | 4.49 | 8.61 |
| Halothane | 3.28 | 8.24 |
| Sevoflurane | 3.33 | 8.71 |
| Desflurane | 3.28 | 8.94 |
| Isoflurane | 3.28 | 8.58 |
| Enflurane | 3.30 | 8.66 |
| Ether | 3.49 | 8.84 |
| Drinkable alcohols | | |
| Methyl alcohol | 3.40 | 9.26 |
| Ethyl alcohol | 3.33 | 9.51 |
| Metabolites | | |
| Acetone | 3.36 | 8.21 |
| Carbon dioxide | 4.26 | |
| Anti-asthmatic preparations | | 8.53 |
| Essential oils | | |
| Geraniol | 3.45 | 9.44 |
| Citronellal | 3.46 | 9.48 |
| Isopropyl methyl ketone | 3.36 | 8.80 |

The wavelength for the transmission in the second transmission band is obtained as an integral multiple as a higher order of the wavelength range of the first transmission band. Synchronously with the signal pattern of this control voltage, two radiation sources are activated such that a first radiation source emits light during a first ramp of the control voltage and a second radiation source emits light during a second ramp of the control voltage.

After passing through the dual-band Fabry-Perot interferometer, the signals are detected by a detector unit and sent to a control and analyzing unit. The lock-in method is preferably used to analyze the signals detected by the detector unit. To use the lock-in method, the radiation sources and/or control voltage are modulated with a modulation frequency. The modulation frequency is made available as a reference signal for the control and analyzing unit for the use of the lock-in method. The principle of a lock-in method is described as prior art, for example, in U.S. Pat. No. 5,477,051.

U.S. Pat. No. 5,477,051 describes an application for obtaining information from modulated light. FIG. 9 of U.S. Pat. No. 5,477,051 shows the necessary components. U.S. Pat. No. 5,477,051 shall be considered to be part of the present invention concerning the signal analysis according to the lock-in method (U.S. Pat. No. 5,477,051 is hereby incorporated by reference in its entirety).

In a first preferred embodiment, a first radiation source and a second radiation source are synchronized with the control voltage of the dual-band Fabry-Perot interferometer. The first radiation source emits a light of a first spectral wavelength, and the second radiation source emits light of a second spectral wavelength. The first ramp of the control voltage is synchronized with the switching on of a first radiation source, and the second ramp of the control voltage is synchronized with the switching-on of the second radiation source. Synchronization with the control voltage is defined in the sense of this invention as a mutual switchover of the radiation sources, where the mutual switchover also comprises a temporary switching on or switching off of both radiation sources. A mutual switchover between two radiation sources is also covered by the present invention if the radiation sources are alternatingly darkened and again released or if the light beams of the radiation sources reach the dual-band Fabry-Perot interferometer through optical closing systems or diaphragm systems such as slit diaphragms, pin diaphragms or through rotating diaphragm wheels and these optical closing systems or diaphragm systems are synchronized with the control voltage of the dual-band Fabry-Perot interferometer. The alternation of the tuned spectral transmission band covers in the sense of this invention a mutual switching of the radiation sources at the time of a particular ramp of the control voltage from a lower voltage level to an upper voltage level, but also at the time of a start of a ramp of the control voltage from an upper voltage level to a lower voltage level.

The beginning of the first ramp of the control voltage is delayed relative to the activation of the first radiation source by a first delay time, which corresponds to the fall time of the second radiation source and to the build-up time of the first radiation source, and the beginning of the second ramp of the control voltage is delayed relative to the activation of the second radiation source by a second delay time, which corresponds to the fall time of the first radiation source and to the build-up time of the second radiation source. The first and second delay times are set preferably in the form of a time constant. The time constant is defined here as the value at which a value of, for example, 63% or 95% of the final value is reached in case of a continuous or exponentially rising or falling curve or as the time interval within which a continuous or exponentially rising or falling curve sweeps the range of values from 10% of the final value to 90% of the final value.

This first embodiment avoids the beginning of a measuring cycle before the first and/or second radiation source has reached the spectral intensity necessary for the measurement. When using thermal radiation sources, in particular, the necessary spectral intensity is reached only after a typical delay time of 80 msec to 150 msec. The build-up times and the fall times of thermal radiation sources are typically in the range of 80 msec to 150 msec and the heating and cooling time constants at room temperature are symmetrical in case of radiation sources of identical design.

In a second preferred embodiment, the second radiation source is activated simultaneously with the switching off of the first radiation source, so that the cooling process of the first radiation source is terminated simultaneously with the end of the heating process of the second radiation source. The same behavior applies to the switchover of from the second radiation source to the first radiation source, the cooling process of the second radiation source being terminated simultaneously with the end of the heating process of the first radiation source.

The typical build-up time is in the range from 80 msec to 150 msec when using thermal radiation sources. A time interval of 75 msec to 175 msec is typically needed for tuning the wavelength range of the dual-band Fabry-Perot interferometer with the control voltage. The mean typical rate of measurement that can be reached for performing the first embodiment variant in the measuring operation is thus obtained as 2 Hz.

In a third preferred embodiment, the first ramp of the control voltage is designed as a control voltage rising linearly and in a ramp-like manner and the second ramp of the control voltage as a control voltage sloping linearly and in a ramp-like manner. A spectral transmission of the dual-band Fabry-Perot interferometer in the first and second transmission bands of the dual-band Fabry-Perot interferometer is associated with each value of the control voltage of the rising ramp and listed in a table as a first transmission data set.

A spectral transmission of the first transmission band and in the second transmission band is associated with each value of the control voltage of the sloping ramp and is listed in the table as a second transmission data set. It is thus possible to use the rising ramp and the sloping ramp to detect valid measured values and not to leave a time period of the control voltage unused. A possible hysteresis in the assignment of the parameters control voltage and spectral transmission of the dual-band Fabry-Perot interferometer is shown by the first and second transmission data sets in the table and has no adverse effect on the gas concentration measurement.

Both the rising ramp (forward scan) and the sloping ramp (backward scan) can be used for the measurement without leaving a time period unused. This ultimately leads to a compensation of the hysteresis of the dual-band Fabry-Perot interferometer and to an increase in the rate of measurement, which is associated therewith, such that the measurement of breathing gases can be resolved for individual phases of breathing.

In a fourth preferred embodiment the second embodiment is varied in terms of the time course such that the beginning of the rise of the control voltage is delayed in relation to the activation of the first radiation source by a delay time T01, which corresponds to the sum of the fall time T22 of the second radiation source and to the build-up time T11 of the first radiation source. The beginning of the drop of the control voltage is delayed in relation to the activation of the second radiation source in this fourth preferred embodiment by a delay time T02, which corresponds to the sum of the fall time T21 of the first radiation source and the build-up time T12 of the second radiation source.

In a fifth embodiment, the resistance values of the first and second radiation sources are detected by means of a voltage and current measurement. The current and voltage measurement is typically used in a gas concentration-measuring device to recognize malfunctions of the radiation source and to avoid unacceptable heating currents. The temperature of the radiation source can be directly inferred from the resistance of the radiation source and the resistance is typically used to regulate the temperature of the radiation source and to avoid excessively high temperatures of the radiation sources.

After switching off, the change in the resistance of the radiation source represents an indicator of the extent by which the radiation source has cooled.

The change in resistance is preferably standardized before the comparison with a predetermined value by forming a relative change in resistance for cooling relative to the resistance value of the active hot radiation source before the active radiation source is switched off and by forming a relative change in resistance for heating relative to the resistance value of the inactive cold radiation source at the beginning of the heating phase. This standardization can be represented according to Formulas 1 and 2.

$$\Delta R_{relativ\_c} = \frac{\Delta R_{relativ}}{R_{cold}} \quad (1)$$

$$\Delta R_{relativ\_H} = \frac{\Delta R_{relativ}}{R_{hot}} \quad (2)$$

By means of this standardization of the change in resistance, the process becomes independent from the types of the radiation sources and from dispersions among individual units within the type, as well as from the effect of the ambient temperature. The inertia of the radiation source is taken into account in this process according to the fourth embodiment both in the actuation of the radiation sources and in the actuation of the dual-band Fabry-Perot interferometer. Furthermore, the standardization of the change in resistance makes it possible to store in the measuring system the predetermined values likewise as standardized predetermined values independently from the particular type of radiation source and the ambient temperature. Due to the change in resistance being included, the rate of measurement is independent from preset typical delay time values of the radiation sources.

If the relative change in resistance drops below a predetermined threshold value, the cooling process is more or less concluded. The relative change in resistance after switching on is likewise an indicator of the extent to which the radiation source has reached the final value of the maximum radiation, and the end of the heating process can also be inferred here from the circumstance that the relative change in resistance has dropped below a predetermined value.

The change in resistance can be typically determined as a first mathematical derivative of the resistance value as a function of time.

In conjunction with the first or third embodiment, this fifth embodiment offers the advantage that the necessary delay time does not have to be determined empirically in experiments and preset as a systematic fixed delay time in the measuring system on the basis of these experiments, but the delay time is obtained adaptively by means of the measurement of the resistance values of the radiation source and of the change in resistance determined therefrom relative to previous measured resistance values.

The ramps of the control voltage are started in this fifth embodiment only when both the change in the resistance of the cooling radiation source and the change in the resistance of the radiation source being heated have each dropped below a first predetermined value for the cooling and a second predetermined value for the heating of the radiation sources.

In another preferred sixth embodiment, the control voltage of the dual-band Fabry-Perot interferometer is used according to the third exemplary embodiment as a rising and again sloping ramp function, and the delay time between the respective active time periods of the first and second radiation sources is prolonged compared to the third exemplary embodiment. The cooling of one radiation source does not take place simultaneously with the heating of the other radiation source in this sixth embodiment, as in the second preferred embodiment. This sixth embodiment according to the present invention makes it possible to check the measuring system. This checking begins with a measurement of reference value data sets without the effect of a target gas to determine the system properties of the dual-band Fabry-Perot interferometer. The process starts with the activation of the first radiation source and of the rising ramp of the control voltage. Before activation of the first radiation source and before the beginning of the rise of the control voltage for the dual-band Fabry-Perot interferometer, the signal of the at least first optical detector is detected as a first reference value data set X1 at a minimal value of the control voltage, which comprises the dark signal components for the first and second spectral transmission bands, and is stored in a memory. The dual-band Fabry-Perot interferometer is subsequently tuned over the spectral range with the rising ramp of the control voltage until the end point of the rising ramp of the control voltage and the signals of the at least first optical detector are detected. This is followed by a waiting period until the previous first active radiation source cools, where the comparison of the standardized change in resistance according to Formula 1 with a predetermined limit value is used to determine the end of cooling of the first radiation source, after which the signal of the at least first optical detector is received as a second reference value data set X2 with the radiation sources switched off at a maximum of the control voltage of the dual-band Fabry-Perot interferometer, which comprises the dark signal components for the first and second spectral transmission bands, and is stored in a memory. With the radiation sources switched off and inactive, the reference value data sets X1 and X2 are characteristic of the background radiation present in the arrangement and the transmission characteristic of the dual-band Fabry-Perot interferometer without the effect of gas absorption of the target gas.

The background radiation determines the noise properties of the measuring arrangement and is an indicator of the temperature of the arrangement, on the one hand, and is, moreover, suitable for deriving therefrom settings for the operation of the dual-band Fabry-Perot interferometer, the radiation sources and the electronic analyzing unit, such as a setting of the amplifier stages. After this reception of the system properties without the effect of a target gas, operation is switched over to the measuring operation by the target gas being fed to the measuring system. The previously inactive second radiation source is activated and time is allowed for heating it up by using the comparison of the standardized change in resistance according to Formula 2 with a predetermined limit value to determine the end of heating of the second radiation source. The dual-band Fabry-Perot interferometer is subsequently tuned with the sloping ramp of the control voltage over the spectral range and the signals of the at least first optical detector are detected and the second radiation source is deactivated simultaneously with the reaching of the minimum of the control voltage.

Time is in turn allowed in the next step for the cooling of the previously active second radiation source, and the comparison of the standardized change in resistance according to Formula 1 with a predetermined limit value is used to determine the end of cooling, after which the signal of the at least first optical detector is received as a current first dark value data set X11 with the radiation sources switched off at a minimum of the control voltage of the dual-band Fabry-Perot interferometer, which data set comprises the dark signal components for the first and second spectral transmission bands, and is stored in a memory. A current second dark value data set X22 is correspondingly recorded in the course of the further operation with the radiation sources switched off at a maximum of the control voltage of the dual-band Fabry-Perot interferometer, which data set comprises the dark signal components for the first and second spectral transmission bands, and is stored in a memory. With the radiation sources switched off and inactive, the dark value data sets X11 and X22 are characteristic of the transmission characteristic of the dual-band Fabry-Perot interferometer under the effect of gas absorption.

Information can be obtained from the comparison of the reference value data sets X1 and X2 and dark value data sets X11 and X22 on the hysteresis of the control voltage and on the change over time in the association with the spectral transmission of the dual-band Fabry-Perot interferometer and on changes in the hysteresis of the control voltage in the association with the spectral transmission.

Both the first and second transmission data sets as well as the reference value data sets X1 and X2 are advantageously determined for this, for the first time at the time of the factory calibration, and, to form a comparison, the quotients $Q1_1$ through $Q1_n$ are subsequently formed in a continuous manner for both spectral transmission bands for the first wavelength range and the quotients $Q2_1$ through $Q2_n$ are formed for the second wavelength range from X1 and X2, as well as continuously for the current dark value data sets X11 and X22, and the changes in the quotients are recorded continuously. If a deviation can be detected between the first quotient $Q1_1$ or $Q2_1$ and a following quotient $Q1_n$ or $Q2_n$, a change in the hysteresis of the transmission characteristic in relation to the control voltage can be inferred from this. A relationship can then be determined from the control voltage and the wavelength for the dual-band Fabry-Perot interferometer by applying Planck's law of radiation according to Formula 3 and using the expression according to Formula 4 for a curve compensation calculation.

$$S \sim dP \sim \frac{const}{\lambda^5 \cdot e^{\frac{hc}{k \cdot \lambda \cdot T}} - 1} \quad (3)$$

$$\lambda = f(U) \quad (4)$$

This relationship can be applied for the further measuring operation by the newly calculated spectral transmission of the dual-band Fabry-Perot interferometer updating the first and second transmission data sets. Further variants for the analysis of the change in hysteresis is the follow-up and determination of the course of a shift of the maxima in the absorption bands of the first and second spectral transmission bands or the use of characteristic emission collapses in the spectrum of the radiation sources compared to the spectrum that the radiation sources usually have and whose spectrum has been recorded during the factory calibration in connection with the first recording of the reference value data sets X1 and X2.

Monitoring of the signal-to-noise ratio of the measured signals, for example, by relating the particular, currently detected measured signals to the reference value data sets X1 and X2 and dark value data sets X11 and X22, makes it possible to recognize defective states of the system. It is thus possible to detect possible defects and drift effects of the components, for example, of the electronic measuring system with a signal processing unit, as well as damage to or contamination of the optical elements or of one radiation source or both radiation sources, contaminations in the measuring gas cell or the dual-band Fabry-Perot interferometer in case of great deviations between X11 and X22 or $Q1_n$ and $Q2_n$, of predetermined threshold values or the reference value data sets X1 and X2.

This sixth embodiment variant describes a system check, which can be performed at the beginning of start-up, but also during the running operation. Due to the measuring time needed in this sixth embodiment for the determination of the reference value data sets X1 and X2 with the optical detector or the fact that the heating of one radiation source cannot take place simultaneously with the cooling of the other radiation source, a longer measuring time is obtained compared to the fourth and fifth embodiments. The mean typical duration for carrying out the system check is obtained from the typical build-up time of the thermal radiation sources in the range of 80 msec to 150 msec and from the time interval of 75 msec to 175 msec needed for the tuning of the wavelength range of the dual-band Fabry-Perot interferometer by means of the control voltage when a necessary measuring time in the range of 20 msec to 40 msec for the detection of the reference value data sets X1 and X2 is assumed. The duration of the measuring time is determined essentially by the signal-to-noise properties of the detectors and of the subsequent signal amplification and the number of measured values for forming the mean value, which number depends thereon. The mean rate of measurement that can be reached for carrying out the sixth embodiment variant in continuous operation is thus found to be 1 Hz.

In a seventh embodiment variant, the system check is applied periodically at predetermined time intervals according to the sixth embodiment variant, while the first, second, third, fourth or fifth embodiment variant is applied in the measuring operation.

A predetermined number of cycles are run at the beginning of measurement with the process according to the fifth embodiment variant. The reference value data sets X1 and X2 are averaged and stored in the memory. Due to the measuring time needed for the system check for the determination of the reference value data sets X1 and X2 in the sixth embodiment and the fact that the heating of one radiation source cannot take place simultaneously with the cooling of the other radiation source, a measuring time is obtained that is longer than in embodiments one through five. The slower rate of measurement according to the sixth embodiment is not acceptable for the gas concentration measurement especially in case of an application in which the measured values shall be obtained in the breathing cycle of newborn and premature babies. Continuous system check is therefore dispensed with in such an application in favor of a faster rate of measurement. The system check is performed in this case before the beginning of the measuring operation and is performed as needed or at regular intervals in the range of about 30-60 minutes or also at intervals of 4 hours in the continuous measuring operation as a function of the particular application and the measuring accuracy needed in order to compensate drift effects.

The changeover to system check in the measuring operation may be the result of a monitoring of the signal-to-noise ratios of the measured signals relative to the reference and dark value data sets X1, X2, X11, X22 or predetermined limit values.

The best possible and fastest possible rate of measurement can thus be guaranteed for the measuring operation and, in addition, periodic checking of the measuring system can be performed.

In an eighth preferred embodiment, the ramp time of the control voltage, which is used to tune the larger wavelength range, is prolonged in such a way that the different spectral spread of the first and second transmission bands of the dual-band Fabry-Perot interferometer is compensated. If, for example, a first wavelength range of $\Delta\lambda_1=4$ μm to 6 μm is tuned for a first duration through the rising ramp of the control voltage, the duration of the sloping ramp will be selected to be twice as long for the tuning of the second wavelength range of $\Delta\lambda_2=8$ μm to 12 μm as the duration of the first duration. The intervals during which a spectral component can be detected by the detector are thus of equal length for both wavelength ranges, and the scanning of the measured values takes place in this manner equidistantly in time and with an equal number of measured values for both wavelength ranges, without having to vary the frequency of scanning.

The eight preferred embodiments are preferably used in the field of application of anesthesia in a use for measuring and monitoring laughing gas, carbon dioxide and inhalation anesthetics in the breathing gas and/or breathing circuit of an anesthesia apparatus. Use in the presence of alcohol compounds in the breathing gas of a person in the field of anesthesia is another preferred application. An alternative use of the eight preferred embodiments is in the area of alcohol concentration measurement for determining the fitness to drive in road traffic or of alcohol concentration measurement for determining the fitness to work in business for work activities that may be hazardous.

Exemplary embodiments of the present invention are shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
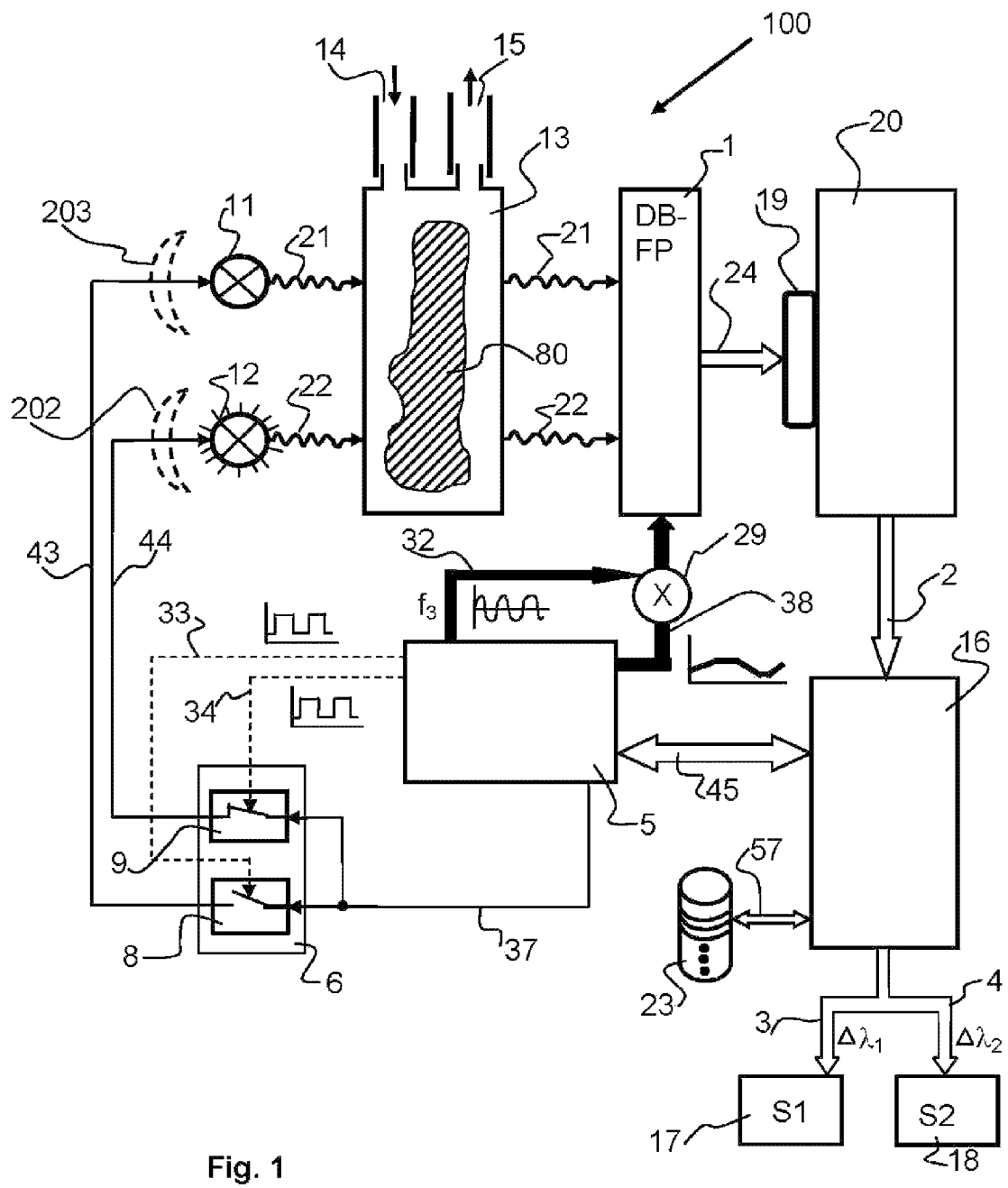
FIG. 1 is a schematic view showing a first gas-measuring device with a dual-band Fabry-Perot interferometer with means for modulating the control voltage of the dual-band Fabry-Perot interferometer.

Referring to the drawings in particular, FIG. 1 schematically illustrates a first gas-measuring device 100 with the dual-band Fabry-Perot interferometer 1.

The first gas-measuring device 100 contains a first radiation source 11, a second radiation source 12, optical elements 202, 203, a measuring gas cell 13 for the gas sample 80 to be analyzed with a gas inlet 14 and a gas outlet 15, the dual-band Fabry-Perot interferometer 1 with an actuating unit 5, a switching unit 6 with switching elements 8, 9 for activating and deactivating the radiation sources 11, 12, a detector unit 19 with a signal processing unit 20, a third mixer 29 for modulating the control voltage 38, a control and analyzing unit 16 for synchronization 45 of the actuation of the radiation sources 11, 12 with the analysis as well as for separating the measured signals associated with the wavelength ranges and signal outputs 17, 18 for the measured signals associated with the wavelength ranges, and a memory 23 for storing reference and dark value data sets. Signal processing unit 20 is connected to the control and analyzing unit 16 via a first data line 2. Second and third data lines 3, 4 establish a connection between the control and analyzing unit 16 and the signal outputs 17, 18. A fourth data line 57 connects the memory 23 to the control and analyzing unit 16.

The dual-band Fabry-Perot interferometer 1 will hereinafter be called DB-FP interferometer 1. The first radiation source 11 emits light up to a wavelength of about 6 μm. The wavelength range between 4 μm and 6 μm is covered with the first radiation source 11. The second radiation source 12 emits light up to a wavelength of about 15 μm. The wavelength range between 8 μm and 12 μm is covered with the second radiation source 12. The radiation sources 11, 12 are activated by the light switching signals 43, 44. Switching unit 6 is designed to switch the third supply signal 37 made available by actuating unit 5 as light switching signals 43, 44 to the first radiation source 11 and/or to the second radiation source 12. A third modulation frequency [$f_3$] 32 in a range between 11 Hz and 25 Hz is mixed by the actuating unit with the control voltage 38 of the DB-FP interferometer 1 via the third mixer 29 and fed to the dual-band 1. The control voltage 38 is preferably modulated sinusoidally. The quantities of light 21, 22 emitted by the radiation sources 11, 12 enter the measuring gas cell 13 through the gas sample 80 and the DB-FP interferometer 1 to reach detector unit 19. The measured signal 24, which is delivered by detector unit 19 and is amplified by the signal processing unit 20 and filtered, is composed of the quantities of light 21, 22 delivered from the radiation sources 11, 12. The measured signal 24 is processed in the analyzing unit 16 with the inclusion of the light control signals 33, 34. The separation of the absorption lines is preferably performed according to the lock-in principle in the analyzing unit 16, and the measured signal 24 is processed for this, with inclusion of the light control signals 33, 34 and frequency [$f_3$], such that they can be associated with the first wavelength range $\Delta\lambda_1$=4 μm to 6 μm and with the second wavelength range $\Delta\lambda_2$=8 μm to 12 μm and are available at the signal outputs 17, 18 as signals $S_1$ and $S_2$.

Figure 2:
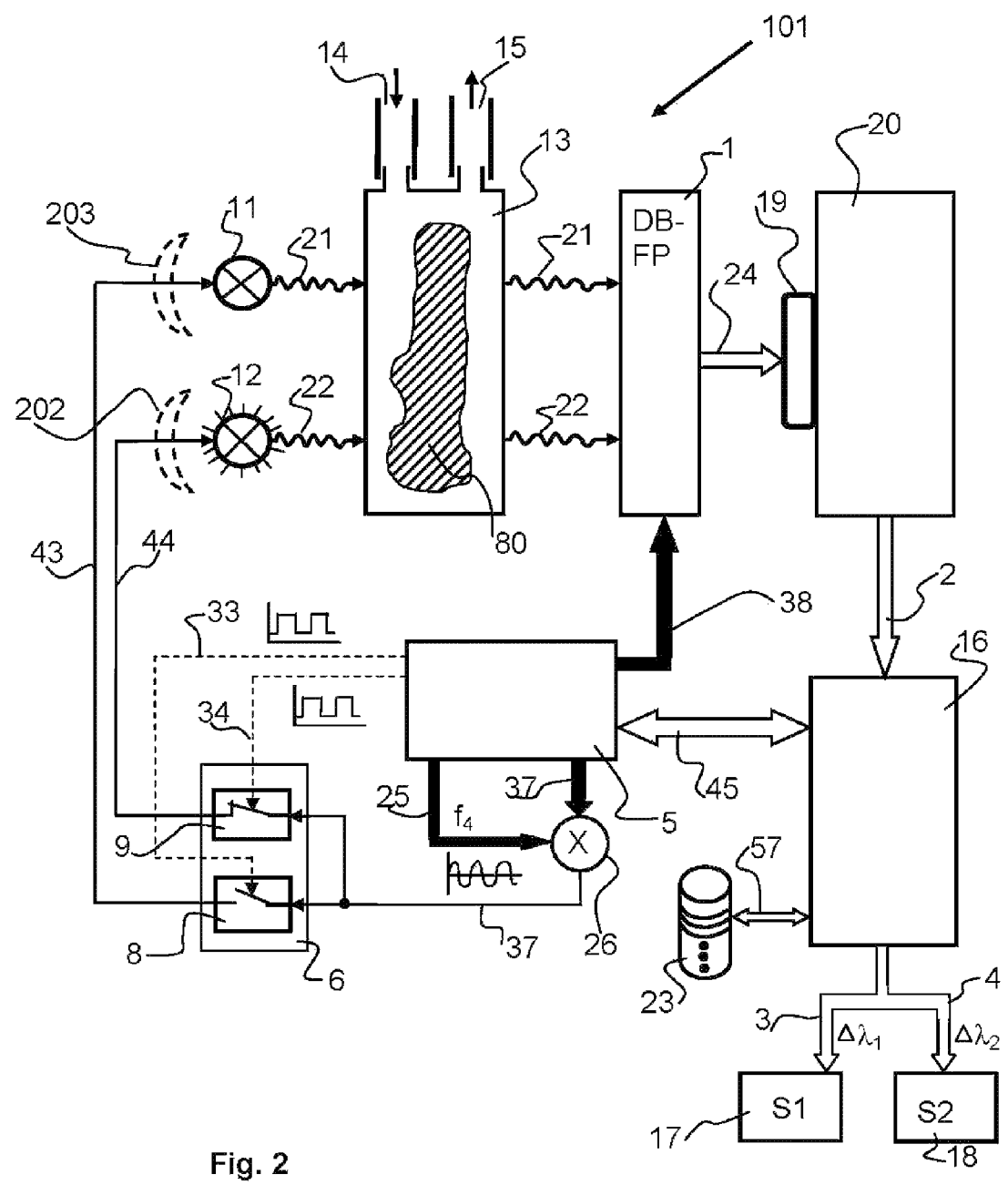
FIG. 2 is a schematic view showing a second gas-measuring device with a dual-band Fabry-Perot interferometer with means for the joint modulation of the radiation sources.

FIG. 2 schematically illustrates a second alternative gas-measuring device 101 with a DB-FP interferometer 1. Identical components are designated by the same reference numbers as in FIG. 1. The second alternative gas-measuring device 101 contains a first radiation source 11, a second radiation source 12, optical elements 202, 203, a measuring gas cell 13 arranged in the infrared optical path for the gas sample 80 to be analyzed with a gas inlet 14 and with a gas outlet 15, the dual-band Fabry-Perot interferometer 1 with an actuating unit 5, a switching unit 6 with switching elements 8, 9 for activating and deactivating the radiation sources 11, 12, a detector unit 19 with a signal processing unit 20, a fourth mixer 26 for modulating the third supply signal 37, a control and analyzing unit 16 for synchronization 45 of the actuating unit of the radiation sources 11, 12 with the analysis, as well as for separating the measured signals associated with the wavelength ranges and signal outputs 17, 18 for the measured signals associated with the wavelength ranges and a memory 23 for storing reference and dark value data sets. The signal processing unit 20 is connected to the control and analyzing unit 16 via a data line 2. Second and third data lines 3, 4 establish a connection between the control and analyzing unit 16 and the signal outputs 17, 18. A fourth data line 57 connects the memory 23 to the control and analyzing unit 16. The first radiation source 11 emits light up to a wavelength of about 6 μm. The wavelength range between 4 μm and 6 μm is covered with the first radiation source 11. The second radiation source 12 emits light up to a wavelength of about 15 μm. The wavelength range between 8 μm and 12 μm is covered with the second radiation source 12. The radiation sources 11, 12 are activated by the light switching signals 43, 44. The switching unit 6 is designed to switch the third supply signal 37 made available by the actuating unit 5 as a light switching signal 43, 44 to the first radiation source 11 and/or to the second radiation source 12. The modulation frequency [$f_4$] 25 for the radiation sources 11, 12 is in a range between 11 Hz and 25 Hz and is mixed with the third supply signal 37 via a fourth mixer 26. The third supply voltage 37 is preferably modulated sinusoidally. The control voltage 38 is fed by the actuating unit 5 to the DB-FP interferometer 1. The quantities of light 21, 22 emitted by the radiation sources 11, 12 enter the measuring gas cell 13 through the gas sample 80 and the DB-FP interferometer 1 to reach detector unit 19. The measured signal 24, delivered by detector unit 19, amplified by the signal processing unit 20 and filtered, is based on the quantities of light 21, 22 delivered by the radiation sources 11, 12. The measured signal 24 is processed in the analyzing unit 33, 34 with inclusion of the light control signals 33, 34. The separation of the spectral components is preferably performed according to the lock-in principle in the analyzing unit 16; the measured signal 24 is processed for this, with the inclusion of the light control signals 33, 34 and the frequency [$f_4$], such that they can be associated with the wavelength ranges $\Delta\lambda_1$, $\Delta\lambda_2$ and are available as signals $S_1$ and $S_2$ at the signal outputs 17, 18.

Figure 3:
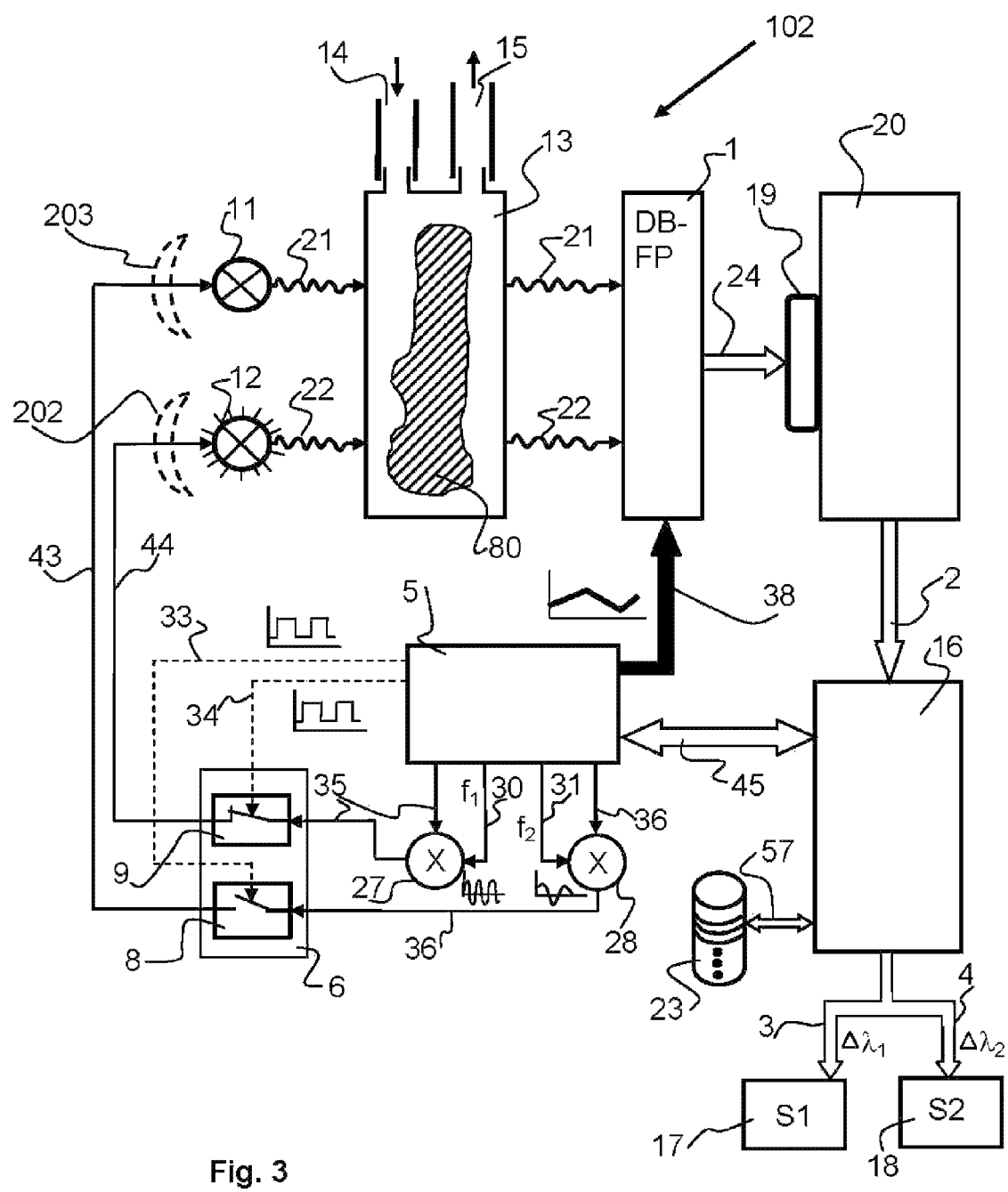
FIG. 3 is a schematic view showing a third gas-measuring device with a dual-band Fabry-Perot interferometer with means for the separate modulation of the radiation sources.

FIG. 3 schematically illustrates a third alternative gas-measuring device 102 with the DB-FP interferometer 1. Identical components are designated by the same reference numbers as in FIG. 1. The third alternative gas-measuring device 102 contains a first radiation source 11, a second radiation source 12, optical elements 202, 203, a measuring gas cell 13 arranged in the infrared optical path for the gas sample 80 to be analyzed with a gas inlet 14 and with a gas outlet 15, the dual-band Fabry-Perot interferometer 1 with an actuating unit 5, a switching unit 6 with switching elements 8, 9 for activating and deactivating the radiation sources 11, 12, a detector unit 19 with a signal processing unit 20, a first mixer 27 and a second mixer 28 for modulating the first and second supply signals 35, 36, a control and analyzing unit 16 for synchronization 45 of the actuation of the radiation sources 11, 12 with the analysis as well as for separating the measured signals associated with the wavelength ranges and signal outputs 17, 18 for the measured signals associated with the wavelength ranges and a memory 23 for storing reference and dark value data sets. The signal processing unit 20 is connected to the control and analyzing unit 16 via a first data line 2. Second and third data lines 3, 4 establish a connection between the control and analyzing unit 16 and the signal outputs 17, 18. A fourth data line 57 connects the memory 23 to the control and analyzing unit 16. The first radiation source 11 emits light up to a wavelength of about 6 μm. The wavelength range between 4 μm and 6 μm is covered with the first radiation source 11. The second radiation source 12 emits light up to a wavelength of about 15 μm. The wavelength range between 8 μm and 12 μm is covered with the second radiation source 12. The radiation sources 11, 12 are activated by the light switching signals 43, 44. A switching unit 6 is designed to switch the first and second supply signals 35, 36 made available by the actuating unit 5 as light switching signals 43, 44 to the first radiation source 11 and/or to the second radiation source 12. The first modulation frequency $f_1$ 30 for the first radiation source 11 is in a range between 11 Hz and 25 Hz and is mixed with the first supply signal 35 via a first mixer 27. The second modulation frequency $f_2$ 31 for the second radiation source 12 is in a range between 51 Hz and 65 Hz and is mixed with the second supply signal 36 via a second mixer 28. The first and second supply signals 35, 36 are preferably modulated sinusoidally. The quantities of light 21, 22 emitted by the radiation sources 11, 12 enter the measuring gas cell 13 through the gas sample 80 and the DB-FP interferometer 1 to reach the detector unit 19. The measured signal 24, delivered by the detector unit 19, amplified by the signal processing unit 20 and filtered, is composed of the quantities of light 21, 22 delivered by the radiation sources 11, 12. The measured signal 24 is processed in the analyzing unit 16 with the inclusion of the light control signals 33, 34. The separation of the spectral components is preferably performed according to the lock-in principle in the analyzing unit 16; the measured signal 24 is processed for this, with inclusion of the light control signals 33, 34 and the first and second modulation frequencies [$f_1$] 30, [$f_2$] 31, such that they can be associated with the wavelength ranges $\Delta\lambda_1$, $\Delta\lambda_2$ and are available as signals $S_1$ and $S_2$ at the signal outputs 17, 18.

FIGS. 4 through 6 and 12 show the courses over time and synchronization of the control voltage 38 with the light switching signals 43, 44 for the radiation sources 11, 12 (FIG. 1) as well as the respective corresponding curves 73, 74 of the ohmic resistance of the radiation sources 11, 12 (FIG. 1) and a spectral curve of the measured signals 50.

Figure 4:
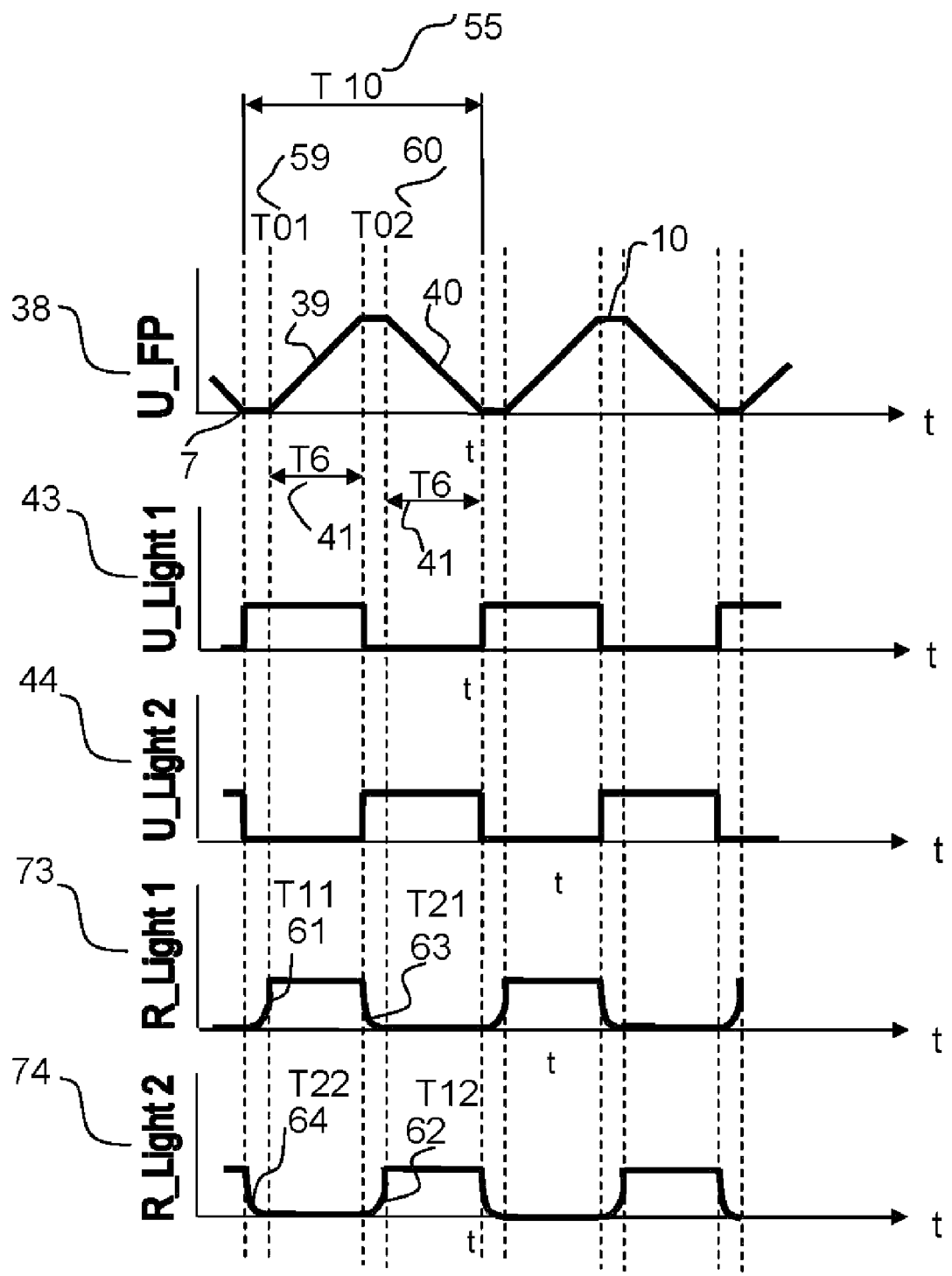
FIG. 4 is a schematic view showing a first time course of a process for operating a dual-band Fabry-Perot interferometer according to FIGS. 1 through 3 and 8.

FIG. 4 shows a first procedure for operating a DB-FP interferometer according to FIG. 1. The curve of the control voltage 38, the resistance curve 73 of the first radiation source 11 (FIG. 1), the resistance curve 74 of the second radiation source 12 (FIG. 1), as well as the curve of the light switching signals 43, 44 are shown. The beginning of a first ramp of the control voltage 38 is delayed relative to the activation of the first radiation source 11 (FIG. 1) by a first delay time [T01] 59, which corresponds to the fall time [T22] 64 of the second radiation source and the build-up time [T11] 61 of the first radiation source 11 (FIG. 1), and the beginning of the second ramp of the control voltage 38 is delayed relative to the activation of the second radiation source 12 (FIG. 1) by a second delay time [T02] 60, which corresponds to the fall time [T21] 63 of the first radiation source and the build-up time [T12] 62 of the second radiation source 12 (FIG. 1). The build-up times [T11] 61, [T12] 62 and fall times [T21] 63, [T22] 64 are in the range of 80 msec to 150 msec in case of a thermal radiation source. The control voltage 38 is raised linearly and continuously in the form of a first ramp 39 from a lower voltage level 7 of 0 V to an upper voltage level 10 of about 30 V. The time [T6] 41 typically needed for the first ramp is in the range of 75 msec to 175 msec. The upper voltage level 10 is maintained for the first delay time [T01] 59 of 80 msec to 150 msec. The control voltage is lowered in the next step from 30 V to a lower voltage level 7 of 0 V with a second ramp 40 of the time [T6] 41 and subsequently maintained for a second delay time [T02] 61 of 80 msec to 150 msec. The time [T6] 41 typically needed for the second ramp 40 is in the range of 75 msec to 175 msec. The determination of the build-up and fall times [T11] 61, [T12] 62, [T21] 63, [T22] 64 and of delay times [T01] 59, [T02] 60 corresponding to the build-up and fall times [T11] 61, [T12] 62, [T21] 63, [T22] 64 is performed by determining the relative change in the resistance of the first and second radiation sources. The voltage and current curves of the first and second radiation sources are detected for this and the relative change in resistance calculated therefrom is compared to a predetermined limit value. If the relative change in the resistance of the first and second radiation sources drops below the predetermined limit value, the first radiation source is cooled insufficiently and the second radiation source has become established at a working temperature and the particular delay time [T01] 61, [T02] 62 has thus ended. The typical build-up times and fall times [T11] 61, [T12] 62, [T21] 63, [T22] 64 are in the range of 80 msec to 150 msec in case of a thermal radiation source. An operating time [T10] 55 of 300 msec to 600 msec is obtained from the delay times [T01] 59, [T02] 60 and the two time periods [T6] 41 of the control voltage. This leads to a rate of measurement in the range of 1.5 Hz to 3 Hz for the operation of the gas concentration-measuring device. Due to the dispersion of the build-up characteristics of the thermal radiation sources among individual units, a lower rate of measurement of 1 Hz to 1.5 Hz can be estimated for a practical application without analysis of the resistance curves 73, 74. The dispersion in the build-up characteristics among individual units of the thermal radiation sources is also taken into account for a practical application with analysis of the resistance curves 73, 74 and the rate of measurement is automatically adjusted to the specific dynamic properties of the thermal radiation sources used in the arrangement, and the maximum typical rate of measurement of 3 Hz can then be used during the operation when using correspondingly selected thermal radiation sources.

Figure 5:
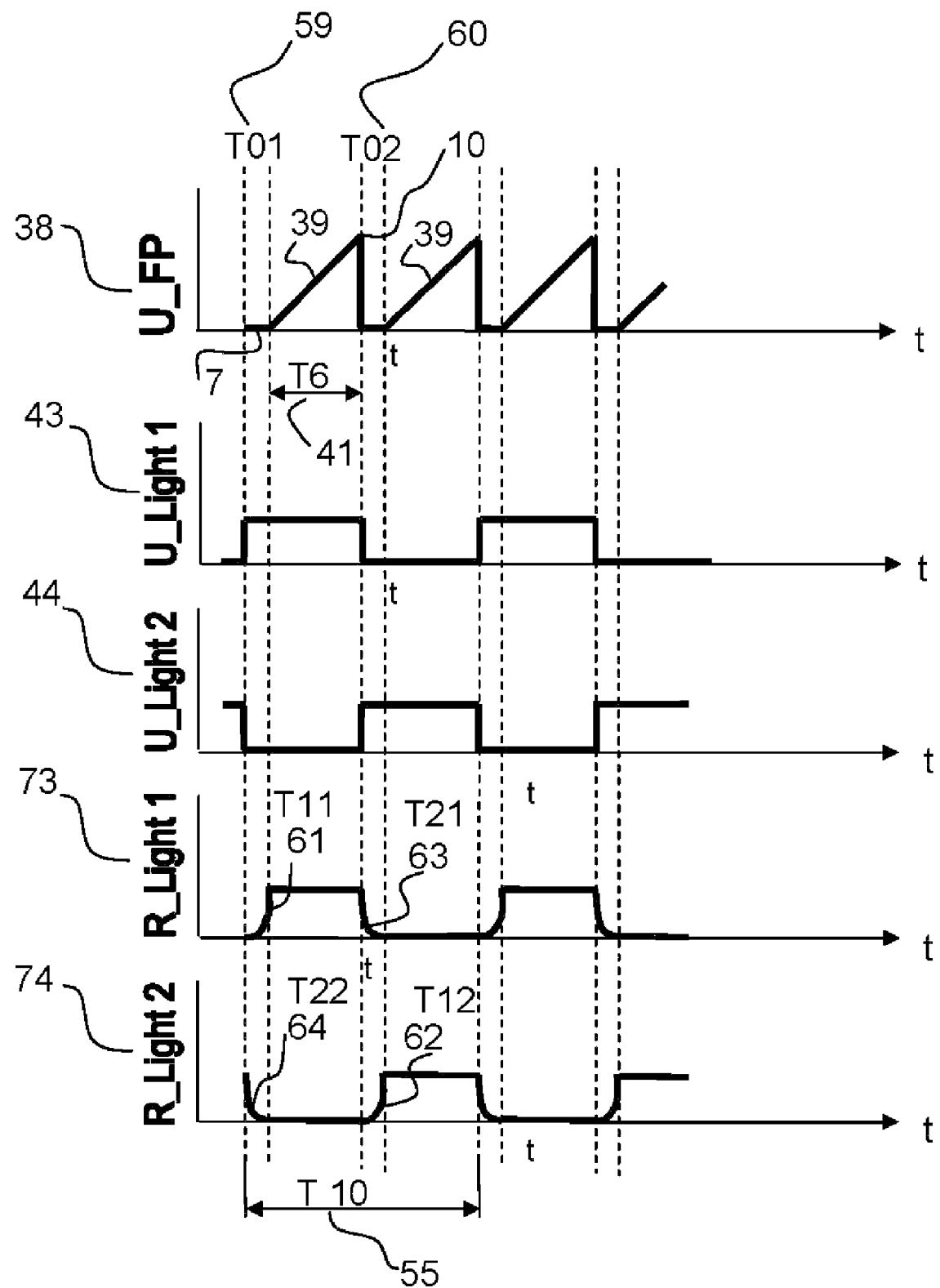
FIG. 5 is a schematic view showing a second time course of a process for operating a dual-band Fabry-Perot interferometer according to FIGS. 1 through 3, 7 and 8.

FIG. 5 shows a second procedure for the operation of a DB-FP interferometer according to FIG. 1. The curve of the control voltage 38, the resistance curve 73 of the first radiation source 11 (FIG. 1), the resistance curve 74 of the second radiation source 12 (FIG. 1), as well as the curve of the light switching signals 43, 44 are shown. The beginning of a ramp of the control voltage 38 is delayed relative to the activation of the radiation sources 11, 12 (FIG. 1) by a first and second delay times [T01] 59, [T02] 60, which correspond to the fall times [T21] 63, [T22] 64 and the build-up times [T11] 61, [T12] 62 of the radiation sources 11, 12 (FIG. 1). The control voltage 38 is raised linearly and continuously in the form of a ramp 39 from a lower voltage level 7 of 0 V to an upper voltage level 10 of about 30 V. The time [T6] 41 typically needed for the first ramp 39 is in the range of 75 msec to 175 msec. The control voltage is lowered in the next step directly from 30 V to a lower voltage level 7 of 0 V and subsequently maintained again for the first delay time [T01] 59 in the range of 80 msec to 150 msec. The determination of the build-up and fall times [T11] 61, [T12] 62, [T21] 63, [T22] 64 and of the delay times [T01] 59, [T02] 60 corresponding to the build-up and fall times [T11] 61, [T12] 62, [T21] 63, [T22] 64 is carried out by determining the relative change in the resistance of the first and second radiation sources. The voltage and current curves of the first and second radiation sources are detected for this and the relative change in resistance calculated therefrom is compared with a predetermined limit value. If the relative change in the resistance of the first and second radiation sources drops below the predetermined limit value, the first radiation source is cooled sufficiently and the second radiation source has stabilized at the working temperature and the particular delay time [T01] 59, [T02] 60 has thus ended. The typical build-up times and fall times [T11] 61, [T12] 62, [T21] 63, [T22] 64 in case of a thermal radiation source are in the range of 80 msec to 150 msec. A typical operating time [T10] 55 of 300 msec to 600 msec is obtained from the delay times [T01] 59, [T02] 60 and the two time periods [T6] 41 of the control voltage. This leads to a rate of measurement in the range of 1.5 Hz to 3 Hz for the operation of the gas concentration-measuring device. Due to the dispersion of the build-up characteristics of the thermal radiation sources among individual units, a lower rate of measurement of 1 Hz to 1.5 Hz can be estimated for a practical application without analysis of the resistance curves 73, 74. The dispersion in the build-up characteristics among individual units of the thermal radiation sources is thus also taken into account for a practical application with analysis of the resistance curves 73, 74 and the rate of measurement is automatically adjusted to the specific dynamic properties of the thermal radiation sources, and the maximum typical rate of measurement of 3 Hz can then be used during the operation when using correspondingly selected thermal radiation sources.

Figure 6:
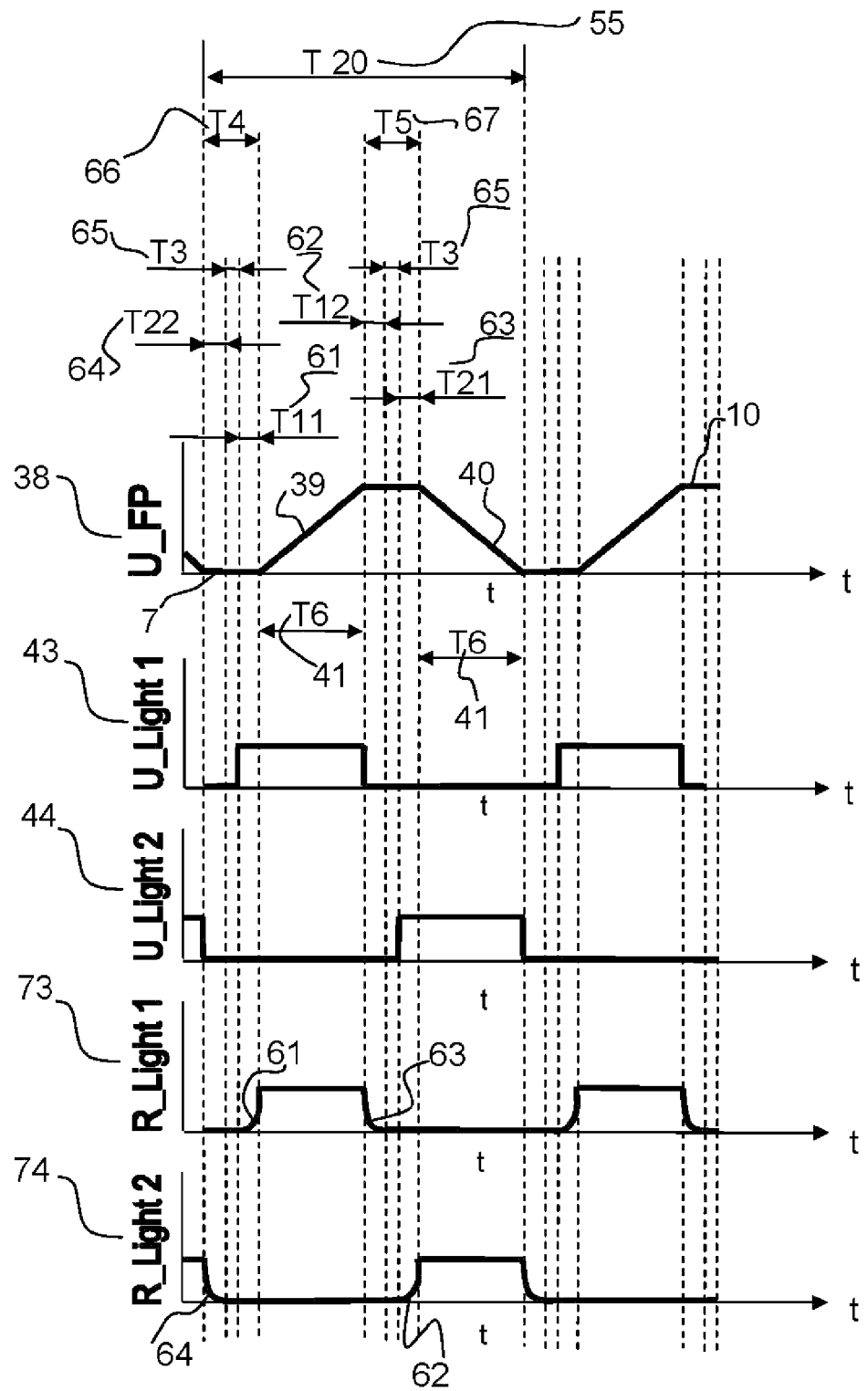
FIG. 6 is a schematic view showing a first view of the course over time of a system check of a dual-band Fabry-Perot interferometer according to FIGS. 1 through 3, 7 and 8.

FIG. 6 shows a first view of the procedure for the system check of a DB-FP interferometer according to FIG. 1. The curve of the control voltage 38, the resistance curve 73 of the first radiation source 11 (FIG. 1), the resistance curve 74 of the second radiation source 12 (FIG. 1), as well as the curve of the light switching signals 43, 44 are shown. The beginning of the first ramp 39 of the control voltage 38 is delayed relative to the activation of the first radiation source 11 (FIG. 1) by a third delay time [T4] 66, which corresponds to the sum of the first build-up time [T11] 61, a measuring time [T3] 65 and the second fall time [T22] 64. The beginning of the second ramp 40 of the control voltage 38 is delayed relative to the activation of the second radiation source 12 (FIG. 1) by a fourth delay time [T5] 67, which corresponds to the sum of the second build-up time [T12] 62, the measuring time [T3] 65 and the first fall time [T21] 63. The control voltage 38 is raised linearly and continuously in the form of a first ramp 39 from a lower voltage level 7 of 0V to an upper voltage level 10 of about 30 V. The time [T6] 41 typically needed for the first ramp 39 is in the range of 75 msec to 175 msec. The upper voltage level 10 is maintained for the duration of the fourth delay time [T5] 67. The duration of the fourth delay time [T5] 67 is composed of the second build-up time [T12] 62 of the second radiation source 12 (FIG. 1), the measuring time [T3] 65 and the first fall time [T21] 63 of the first radiation source 11 (FIG. 1). The control voltage is lowered in the further course with a second ramp 40 with a typically needed time [T6] 41 of 75 msec to 175 msec from the upper voltage level 10 of 30 V to a lower voltage level 7 of 0 V and subsequently maintained again for the third delay time [T4] 66 until the control voltage 38 is again raised linearly and continuously with a rising ramp from a lower voltage level 7 of 0 V to an upper voltage level 10 of about 30 V. The duration of the third delay time [T4] 66 is composed of the first build-up time [T11] 61 of the first radiation source 11 (FIG. 1), the measuring time [T3] 65 and the second fall time [T22] 64 of the second radiation source 12 (FIG. 1). This procedure is continued cyclically. A first reference value data set X1 51 (FIG. 11) at the lower voltage level 7 of the control voltage 38 and a second reference value data set X2 52 (FIG. 11) at the upper voltage level 10 of the control voltage 38 are recorded by the detector unit 19 (FIG. 1) during the measuring times [T3] 65, sent to the control and analyzing unit 16 (FIG. 1) and stored in a memory 23 (FIG. 1). A current first dark value data set X11 53 (FIG. 12) at the lower voltage level 7 of the control voltage 38 and a current second reference value data set X22 54 (FIG. 12) at the upper voltage level 10 of the control voltage 38 are cyclically recorded in the further course, sent to the control and analyzing unit 16 (FIG. 1) and stored in a memory 23 (FIG. 1). The determination of the build-up and fall times [T11] 61, [T12] 62, [T21] 63, [T22] 64 is performed by determining the relative change in the resistance of the first and second radiation sources. The voltage and current curves of the first and second radiation sources are detected for this and the relative change in resistance calculated therefrom is compared with a predetermined limit value. The typical measuring time [T3], which is needed for detecting the first and second reference value data sets X1 51, X2 52 (FIG. 11) or the current dark value data sets X11 53, X22 54 (FIG. 12), is in the range of 20 msec to 40 msec. Typical values for the third and fourth delay times [T4] 66, [T5] 67 are obtained in the range from 180 msec to 360 msec in case of a thermal radiation source when taking [T3] 65 and the build-up and fall times [T11] 61, [T12] 62, [T21] 63, [T22] 64 into account. A checking time [T20] 56 of 500 msec to 1,200 msec is obtained from the two delay times [T4] 66, [T5] 67 and the two time periods [T6] 41 of the ramps of the control voltage 38. This corresponds to a rate of measurement in the range of 0.8 Hz to 2 Hz (Hertz).

Figure 7:
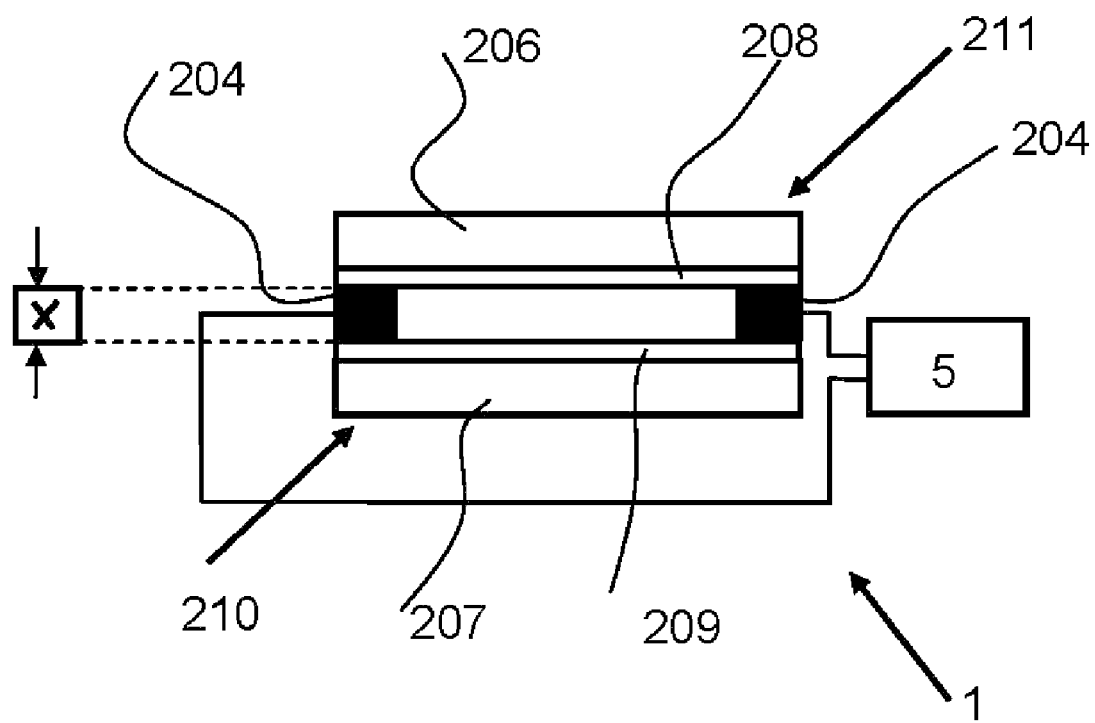
FIG. 7 is a schematic view showing the design of a tunable Fabry-Perot interferometer.

FIG. 7 schematically illustrates the inner structure of the tunable Fabry-Perot interferometer 1 according to FIGS. 1, 2, 3 and 8, in which two mirror surfaces 211, 210 are fixed in parallel to one another by a spacer 204. Spacer 204, which is connected to an actuating unit 5, makes it possible to vary the distance x between the mirrors 211, 210. Mirrors 211, 210 consist of substrates 206, 207, which are provided with reflecting coatings 208, 209 on their surfaces. The transmission properties of the coatings 208, 209 are such that predetermined wavelength ranges can be analyzed. The analyzable wavelength ranges cover the wavelengths between 4 µm and 6 µm as well as between 8 µm and 12 µm.

Figure 8:
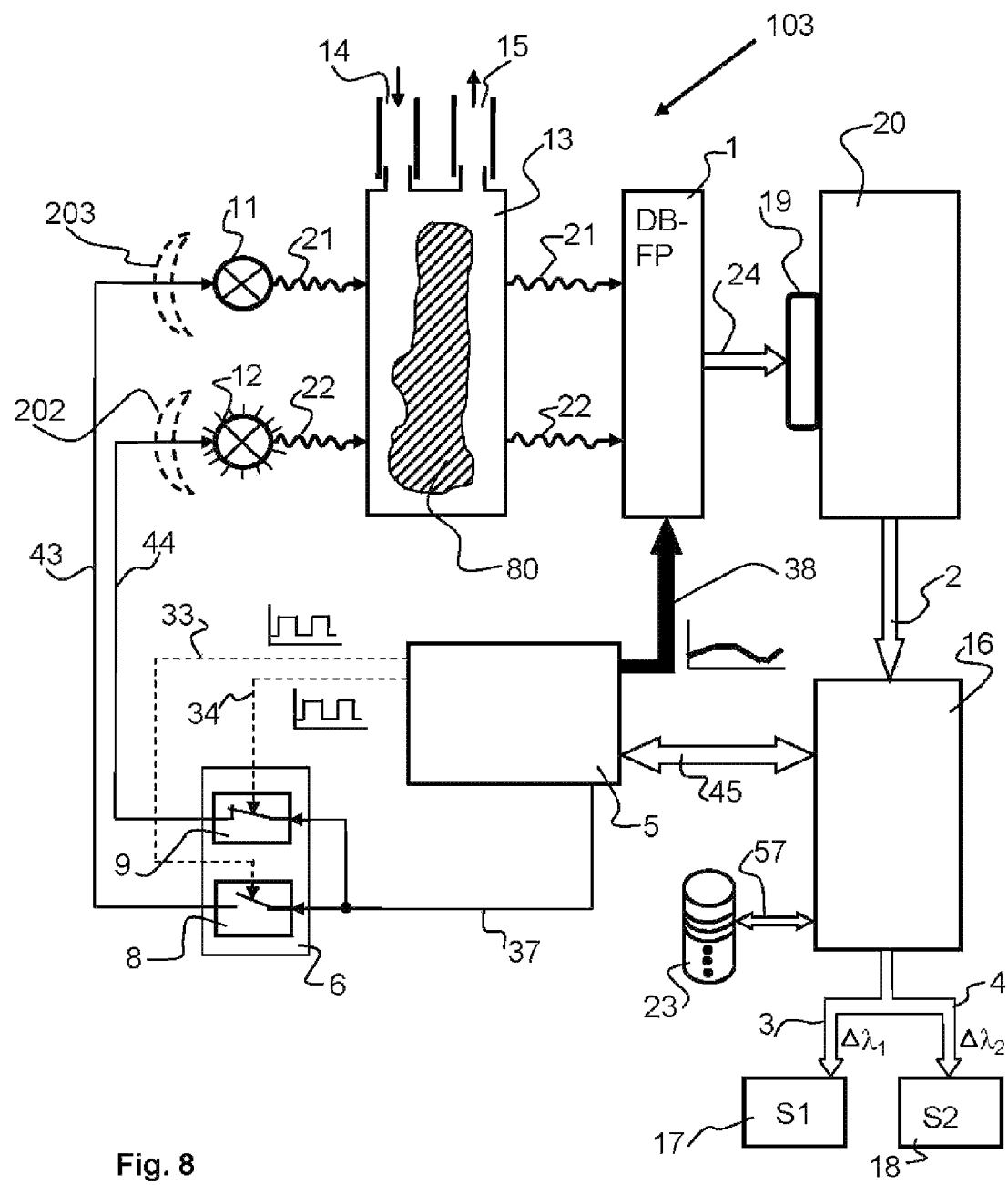
FIG. 8 is a schematic view showing a fourth gas-measuring device with a dual-band Fabry-Perot interferometer without means for modulation.

FIG. 8 schematically illustrates a fourth alternative gas-measuring device 103 with the DB-FP interferometer 1 without modulation of the radiation sources 11, 12 or of the control voltage 38 of the DB-FP interferometer 1. Identical components are designated by the same reference numbers as in FIG. 1. The forth alternative gas-measuring device 102 contains a first radiation source 11, a second radiation source 12, optical elements 202, 203, a measuring gas cell 13 arranged in the infrared optical path for the gas sample 80 to be analyzed with a gas inlet 14 and with a gas outlet 15, the dual-band Fabry-Perot interferometer 1 with an actuating unit 5, a switching unit 6 with switching elements 8, 9 for activating and deactivating the radiation sources 11, 12, a detector unit 19 with a signal processing unit 20, a control and analyzing unit 16 for synchronization 45 of the actuating unit of the radiation sources 11, 12 with the analysis as well as for separating the measured signals associated with the wavelength ranges and signal outputs 17, 18 for the measured signals associated with the wavelength ranges, and a memory 23 for storing reference and dark value data sets. The signal processing unit 20 is connected to the control and analyzing unit 16 via a first data line 2. Second and third data lines 3, 4 establish a connection between the control and analyzing unit 16 and the signal outputs 17, 18. A fourth data line 57 connects memory 23 to the control and analyzing unit 16. The first radiation source 11 emits light up to a wavelength of about 6 μm. The wavelength range between 4 μm and 6 μm is covered with the radiation source 11. The second radiation source 12 emits light up to a wavelength of about 15 μm. The wavelength range between 8 μm to 12 μm is covered with the second radiation source 12. The radiation sources 11, 12 are activated by the light switching signals 43, 44. Switching unit 6 is designed such that the first and second supply signals 35, 36 made available by the actuating unit 5 are switched as light switching signals 43, 44 to the first radiation source 11 and/or the second radiation source 12. The quantities of light 21, 22 emitted by the radiation sources 11, 12 enter the measuring gas cell 13 through the gas sample 80 and the DB-FP interferometer 1 to reach the detector unit 19. The measured signal 24, delivered by the detector unit 19, amplified by the signal processing unit 20 and filtered, is composed of quantities of light 21, 22 delivered from the radiation sources 11, 12. Separation of the spectral components 33, 34 is performed in the analyzing unit 16; the measured signal 24 is processed for this, with inclusion of the light control signals 33, 34, such that they can be associated with the wavelength ranges $\Delta\lambda_1$, $\Delta\lambda_2$ and are available as signals $S_1$ and $S_2$ at the signal outputs 17, 18.

Figure 9:
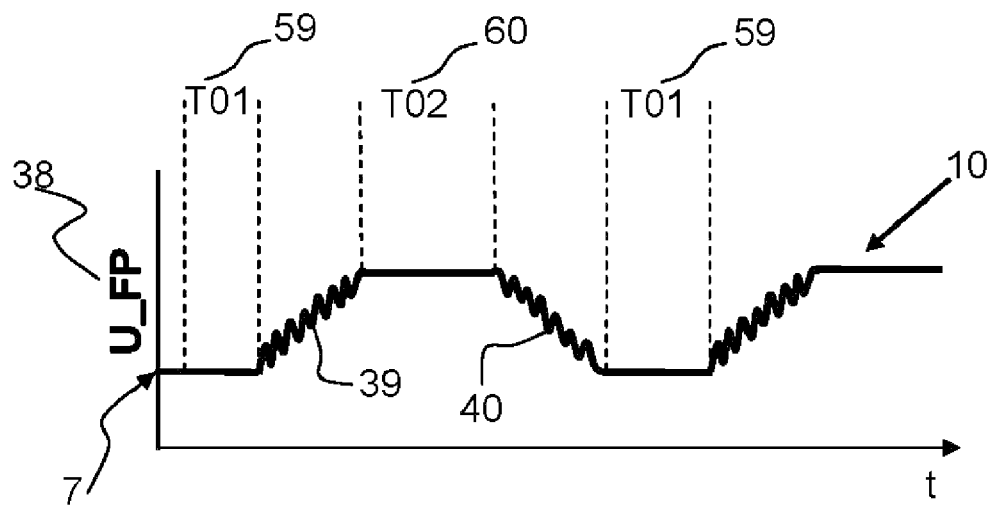
FIG. 9 is a view showing a first variant of a modulated control voltage of the dual-band Fabry-Perot interferometer.

FIG. 9 shows the view of a first variant of a modulated control voltage. The control voltage 38 has, as a function, a lower voltage level 7 for a time period [T01] 59, a rising ramp 39, an upper voltage level 10 for a period [T02] 60 and a sloping ramp 40. Ramps 39, 40 of the control voltage 38 are modulated sinusoidally, and the time periods [T01] 59, [T02] 60 are not modulated and have the horizontal curve of the control voltage 38.

Figure 10:
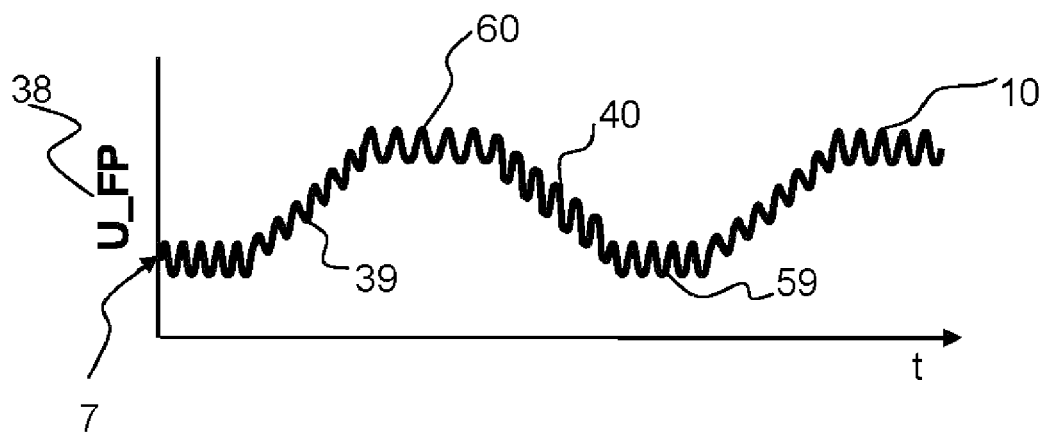
FIG. 10 is a view showing a second variant of a modulated control voltage of the dual-band Fabry-Perot interferometer.

FIG. 10 shows the view of a second variant of a modulated control voltage. The control voltage 38 has, as a function, a lower voltage level 7 for a period [T01] 59, a rising ramp 39, an upper voltage level 10 for a period [T02] 60 and a sloping ramp 40. Both the ramps 39, 40 of the control voltage 38 and the horizontal time periods [T01] 59, [T02] 60 are modulated sinusoidally.

Figure 11:
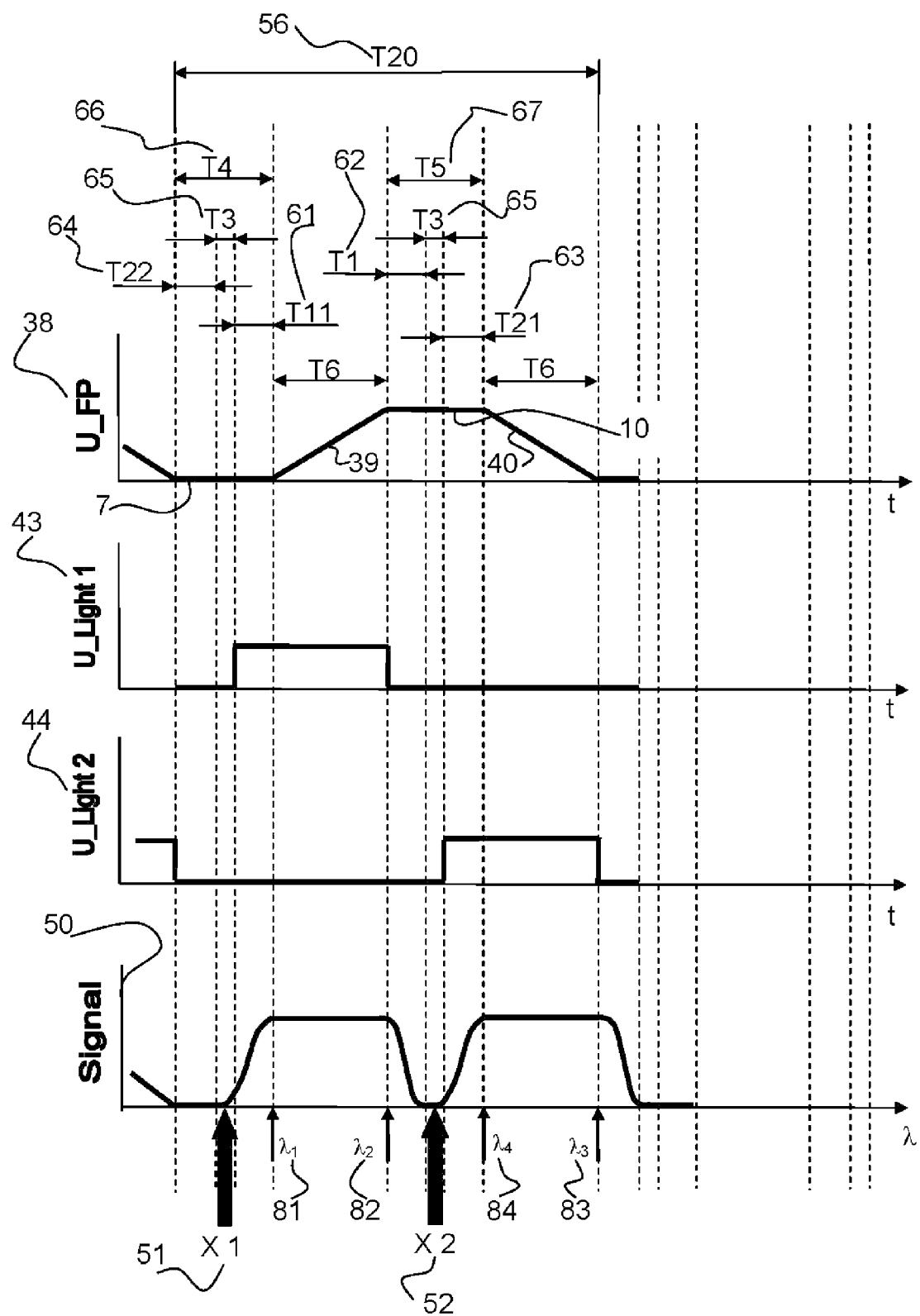
FIG. 11 is a schematic second view of a course over time for the system check of a dual-band Fabry-Perot interferometer according to FIGS. 1 through 3, 7 and 8.

FIG. 11 shows a second view of the procedure of the system check of a DB-FP interferometer according to FIG. 1. The curve of the control voltage 38, the curve of the light switching signals 43, 44 and the spectral curve of the voltage amplitude of the measured signal 50 are shown without the effect of a target gas. The curve of the control voltage 38, the synchronization with the curve of the light switching signals 43, 44 and the designation of the times and elements correspond to the curve and designations of the view in FIG. 6. To determine the system properties, a first reference data set X1 51 is recorded at the lower voltage level 7 of the control voltage 38 during the measuring time [T3] 65 during the third delay time [T4] 66 and a second reference data set X2 52 is recorded at the upper voltage level 10 of the control voltage 38 during the measuring time [T3] 65 during the fourth delay time [T5] 67. A first wavelength range from a first wavelength 81 ($\lambda_1$=4 μm) to a second wavelength 82 ($\lambda_2$=6 μm) is passed over for the ramp time [T6] 61 of the first ramp 39 of the control voltage 38, a second wavelength range from a fourth wavelength 84 ($\lambda_4$=12 μm) to a third wavelength 83 ($\lambda_3$=8 μm) is passed over in the curve of the measured spectral signal 50 for the ramp time [T6] 61 of the second ramp 40 of the control voltage 38, and the curve of the measured spectral signal 50 is recorded.

Figure 12:
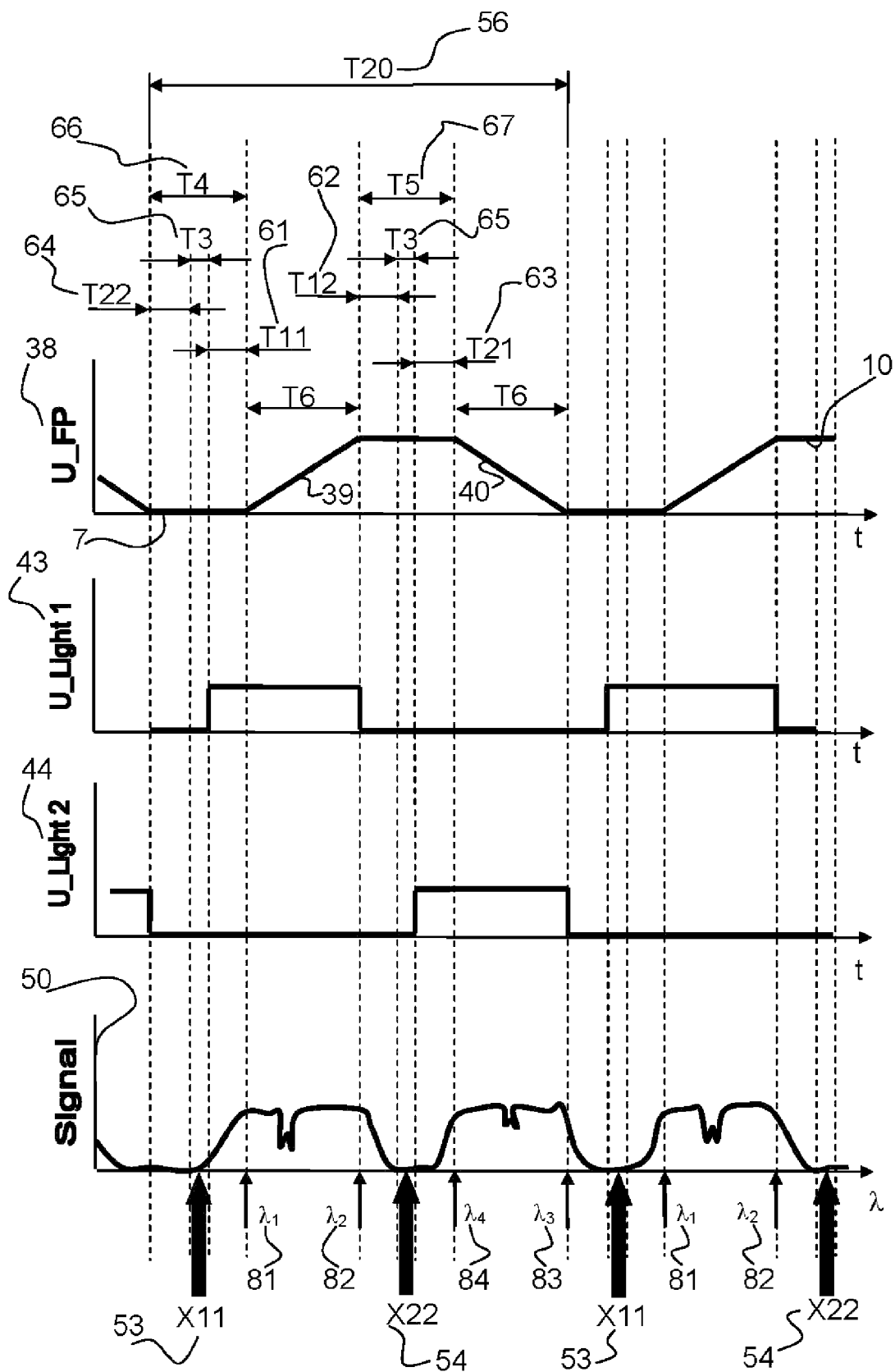
FIG. 12 is a schematic third view of a course over time of a dual-band Fabry-Perot interferometer according to FIGS. 1 through 3, 7 and 8.

FIG. 12 shows a third view of the procedure of the system check of a DB-FP interferometer according to FIG. 1. The curve of the control voltage 38, the curve of the light switching signals 43, 44 and the spectral curve of the voltage amplitude of the measured signal 50 under the effect of a target gas are shown. The curve of the control voltage 38, the synchronization with the curves of the light switching signals 43, 44 and the designation of the times and elements correspond to the curves and designations in the views in FIG. 6. For the continuous determination of the changes in the properties of the system, a first reference data set X11 53 is recorded at the lower voltage level 7 of the control voltage 38 during the measuring time [T3] 65 during the third delay time [T4] 66 and a second reference data set X22 54 is recorded at the upper voltage level 10 of the control voltage 38 during the measuring time [T3] 65 during the fourth delay time [T5] 67. A first wavelength range from a first wavelength 81 ($\lambda_1$=4 μm) to a second wavelength 82 ($\lambda_2$=6 μm) is passed over for the ramp time [T6] 61 of the first ramp 39 of the control voltage 38, a second wavelength range is passed over from a fourth wavelength 84 ($\lambda_4$=12 μm) to a third wavelength 83 ($\lambda_3$=8 μm) in the curve of the measured spectral signal 50 for the ramp time [T6] 61 of the second ramp 40 of the control voltage 38, and the curve of the measured spectral signal 50 is recorded.

Figure 13:
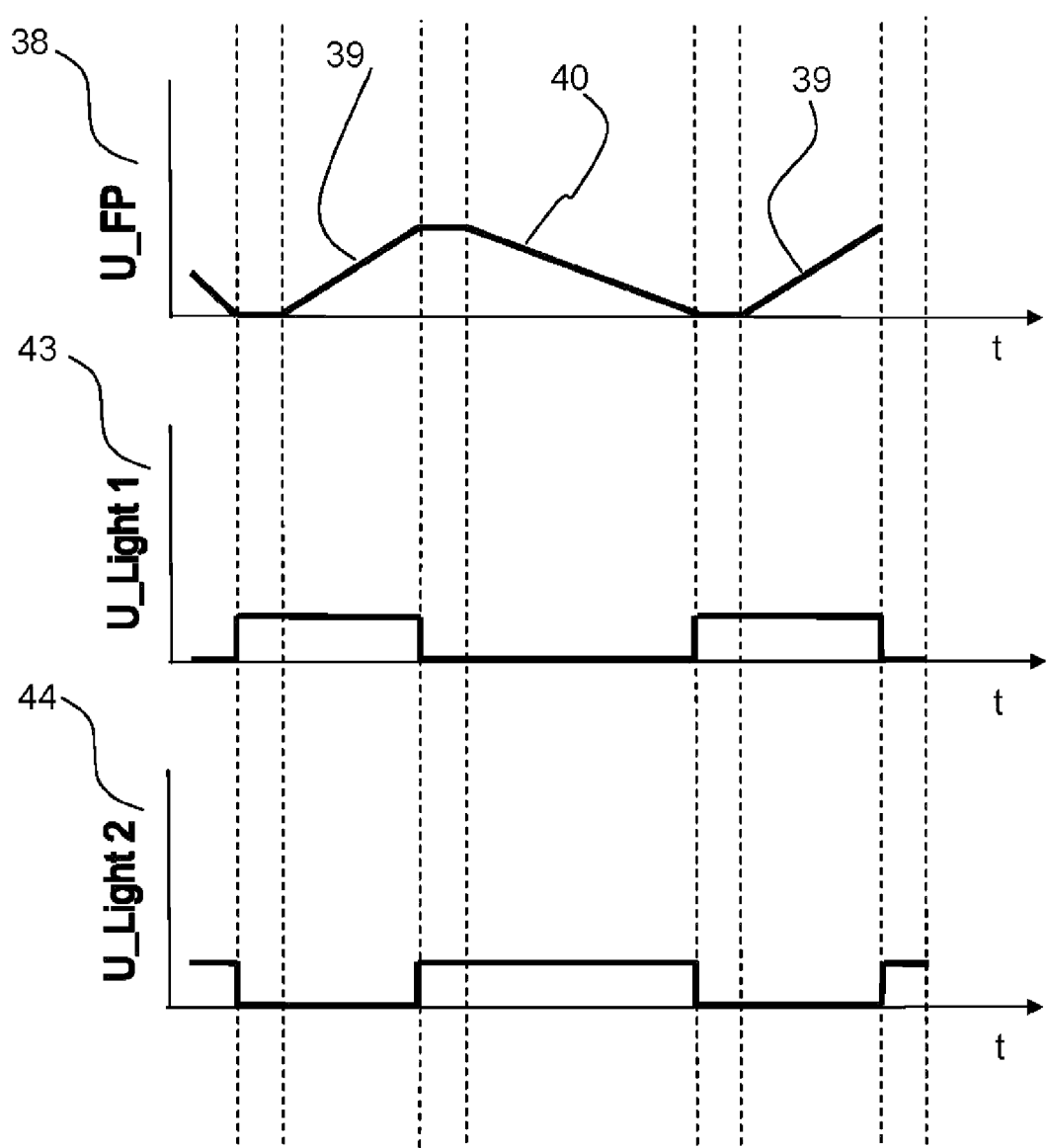
FIG. 13 is a view showing an alternative curve of the control voltage.

FIG. 13 shows an alternative curve of the control voltage 38. The curve of the control voltage 38 and the curves of the light switching signals 43, 44 with a duration of the second ramp 40 of the control voltage 38, which has twice the time of the first ramp 39 of the control voltage 38, are shown. The double time leads to a spectrally equidistant tuning of the DB-FP interferometer 1 in both spectral transmission bands. The wavelength is tuned over a range from 4 μm to 6 μm with a total of $\Delta\lambda$=2 μm during the first ramp 39 of the control voltage 38, and the wavelength is tuned over a range from 8 μm to 12 μm with a total of $\Delta\lambda$=4 μm during the second ramp 40 of the control voltage 38. The tuned wavelength ranges of different size in the first and second transmission bands of the DB-FP interferometer 1 are compensated by the doubling of the time of the second ramp 40 of the control voltage 38 compared to the first ramp 39 of the control voltage 38. The duration during which a spectral component can be detected by detector 19 (FIG. 1) is equal due to the doubling of the time of the second ramp 40 of the control voltage 38 compared to the first ramp 39 of the control voltage 38.

Figure 14:
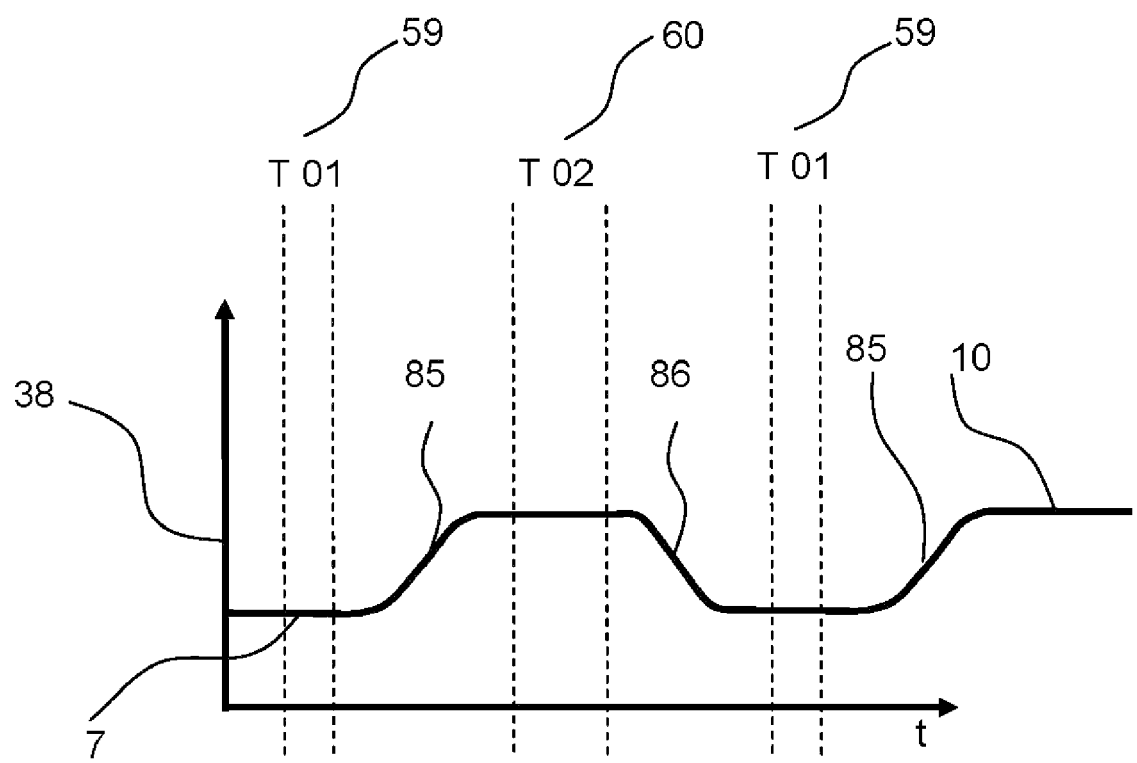
FIG. 14 is a view of a variant of a control voltage with nonlinear sections.

FIG. 14 shows a view of a variant of a control voltage with nonlinear sections. The control voltage 38 has, as a function, a lower voltage level 7 for a time period [T01] 59, a voltage rise 85 to an upper voltage level 10 for a time period [T02] 60 and a voltage drop 86 to the lower voltage level 7. The voltage rise 85 and the voltage drop 86 of the control voltage 38 are in the form of time periods described by nonlinear curves; the voltage levels 7, 10 are maintained as constant values during the time periods [T01] 59, [T02] 60.

While specific embodiments of the invention have been described in detail to illustrate the application of the principles of the invention, it will be understood that the invention may be embodied otherwise without departing from such principles.

| List of Reference Numbers | |
|---|---|
| 1 | DB-FP interferometer |
| 2 | First data line |
| 3 | Second data line |
| 4 | Third data line |
| 5 | Actuating unit |
| 6 | Switching unit |
| 7 | Lower voltage level |
| 8 | First switching element |
| 9 | Second switching element |
| 10 | Upper voltage level |
| 11 | First radiation source |
| 12 | Second radiation source |
| 13 | Measuring gas cell |
| 14 | Gas inlet |
| 15 | Gas outlet |
| 16 | Control and analyzing unit |
| 17, 18 | Signal output |
| 19 | Detector unit |
| 20 | Signal processing unit |
| 21 | First quantity of light |
| 22 | Second quantity of light |
| 23 | Memory |
| 24 | Measured signal |
| 25 | Fourth modulation frequency $f_4$ |
| 26 | Fourth mixer |
| 27 | First mixer |
| 28 | Second mixer |
| 29 | Third mixer |
| 30 | First modulation frequency $f_1$ |
| 31 | Second modulation frequency $f_2$ |
| 32 | Third modulation frequency $f_3$ |
| 33 | First light control signal |
| 34 | Second light control signal |
| 35 | First supply signal |
| 36 | Second supply signal |
| 37 | Third supply signal |
| 38 | Control voltage |
| 39 | First ramp of control voltage |
| 40 | Second ramp of control voltage |
| 41 | Time [T6] of the ramp of the control voltage |
| 43 | First light switching signal |
| 44 | Second light switching signal |
| 45 | Synchronization |
| 50 | Measured signal curve |
| 51 | First reference value data set X1 |
| 52 | Second reference value data set X2 |
| 53 | First dark value data set X11 |
| 54 | Second dark value data set X22 |
| 55 | Operating time [T10] |
| 56 | Checking time [T20] |
| 57 | Fourth data line |
| 59 | First delay time [T01] |
| 60 | Second delay time [T02] |
| 61 | First build-up time [T11] |
| 62 | Second build-up time [T12] |
| 63 | First fall time [T21] |
| 64 | Second fall time [T22] |
| 65 | Measuring time [T3] |
| 66 | Third delay time [T4] |
| 67 | Fourth delay time [T5] |
| 73 | First resistance curve |
| 74 | Second resistance curve |

-continued

| List of Reference Numbers | |
|---|---|
| 80 | Gas sample |
| 81 | First wavelength $\lambda_1$ |
| 82 | Second wavelength $\lambda_2$ |
| 83 | Third wavelength $\lambda_3$ |
| 84 | Fourth wavelength $\lambda_4$ |
| 85 | Voltage rise |
| 86 | Voltage drop |
| 100 | First gas-measuring device |
| 101 | Second gas-measuring device |
| 102 | Third gas-measuring device |
| 103 | Fourth gas-measuring device |
| 202, 203 | Optical elements |
| 204 | Spacer |
| 206, 207 | Substrates |
| 208, 209 | Reflecting coatings |
| 211, 210 | Mirror |

What is claimed is:

1. A process for operating a gas concentration-measuring unit, the process comprising the steps of:
providing the gas concentration-measuring unit with a dual-band Fabry-Perot interferometer, with a first infrared radiation source for a first wavelength range from 4 µm to 6 µm and with a second infrared radiation source for a second wavelength range from 8 µm to 12 µm;
switching the infrared radiation sources on and off by means of light control signals;
tuning the dual-band Fabry-Perot interferometer over a wavelength range by means of a control voltage; and
synchronizing the control voltage with the light control signals.

2. A process in accordance with claim 1, wherein:
a change in the direction of tuning of the dual-band Fabry-Perot interferometer is brought about by means of the control voltage; and
switching is performed between the infrared radiation sources at a time of a change in the direction of tuning of the dual-band Fabry-Perot interferometer.

3. A process in accordance with claim 1, wherein:
tuning of the wavelength range of the dual-band Fabry-Perot interferometer is performed by means of the control voltage;
switching is performed between the infrared radiation sources at the time of a change in the spectral transmission band of the dual-band Fabry-Perot interferometer by means of light control pulses.

4. A process for operating a dual-band Fabry-Perot interferometer, the process comprising the steps of:
providing a dual-band Fabry-Perot interferometer, a first infrared radiation source and a second infrared radiation source;
switching the infrared radiation sources on and off by means of light control signals;
tuning the dual-band Fabry-Perot interferometer over a wavelength by means of a variable ramp function control voltage having a first ramp and a second ramp;
delaying the first ramp of the control voltage relative to a first light switching signal of a first radiation source by a delay time;
delaying the second ramp of the control voltage relative to a second light switching signal of the second radiation source by another delay time; and
providing that the delay time and the another delay time correspond to the respective time constants of the first and second radiation sources.

5. A process according to claim 4, wherein said delay time corresponds to a fall time of the second radiation source and the build-up time of the first radiation source; and said another delay time corresponds to a fall time of the first radiation source and a build-up time of the second radiation source.

6. A process according to claim 4, wherein:
operating the dual-band Fabry-Perot interferometer comprises checking the dual-band Fabry-Perot interferometer; and
said delay time is the sum of a build-up time of the first radiation source, a measuring time and a fall time of the second radiation source and said another delay time is the sum of a build-up time of the second radiation source, a measuring time and a fall time of the first radiation source.

7. A process in accordance with claim 4, wherein the ramps of the control voltage rise and fall linearly in some sections.

8. A process in accordance with claim 1, wherein the control voltage is in a nonlinear form in its entirety or in some sections such that the nonlinearity of the control voltage compensates the transmission characteristic of the dual-band Fabry-Perot interferometer.

9. A process in accordance with claim 8, wherein the nonlinearity of the control voltage is included in the tuning of the dual-band Fabry-Perot interferometer by a mathematical function equation and/or in the form of a table.

10. A process in accordance with claim 4, wherein a relative change in resistance relative to a resistance value of one of the radiation sources after the end of cooling or heating is formed to determine the time of cooling and the time of heating, wherein the relative resistance values are compared with predetermined values and delay times are ended when the values drop below the predetermined values.

11. A process in accordance with claim 4, wherein:
a first reference value data set is detected by a detector unit at a lower voltage level during a measuring time with the radiation sources switched off and the detected first reference value data set is stored in memory;
a second reference value data set is detected by the detector unit at an upper voltage level during the measuring time and the second reference value data set is stored in memory.

12. A process in accordance with claim 4, wherein:
a current first dark value data set is detected by a detector unit at a lower voltage level in a regular sequence during a measuring time with the radiation sources switched off and the current first dark value data set is stored in memory;
a current second dark value data set is detected by the detector unit at an upper voltage level during the measuring time and the current second dark value data set is stored in memory.

13. A process in accordance with claim 11, wherein the first reference value data set is compared with the second reference value data set and the transmission properties of the dual-band Fabry-Perot interferometer are determined from the comparison and stored in memory.

14. A process in accordance with claim 12, wherein:
a first reference value data set is compared with the first dark value data set;
a second reference value data set is compared with the second dark value data set;
the respective current reference value data set is compared in a further sequence with one of the preceding reference and dark value data sets and the transmission properties of the dual-band Fabry-Perot interferometer and the change in the transmission properties of the dual-band Fabry-Perot interferometer are determined continuously and stored in memory.

15. A process in accordance with claim 14, wherein the transmission properties and change in the transmission properties are compared with a predetermined threshold value and the ability of the dual-band Fabry-Perot interferometer of the radiation sources or of the optical elements to function is determined.

16. A process in accordance with claim 1, wherein the control voltage of the dual-band Fabry-Perot interferometer is modulated sinusoidally.

17. A process in accordance with claim 1, wherein the radiation sources are modulated sinusoidally.

18. A process in accordance with claim 1, wherein the control voltage is a ramp function with ramps in the form of nonlinear functions in some sections.

19. A process in accordance with claim 1, wherein the control voltage is a ramp function with a first ramp of the control voltage in the form of a function rising linearly from a lower voltage level to an upper voltage level and wherein a second ramp of the control voltage is in the form of a function sloping linearly from an upper voltage level to a lower voltage level.

20. A process in accordance with claim 1, wherein the control voltage is a ramp function with a function curve of a first ramp of the control voltage in the form of a nonlinear and rising function as a whole or in some sections from a lower voltage level to an upper voltage level and wherein a second ramp of the control voltage is in the form of a nonlinear and falling function as a whole or in some section from an upper voltage level to a lower voltage level.

21. A process in accordance with claim 1, wherein the control voltage is a ramp function with ramp times of the control voltage are selected to be such that an equidistant spectral tuning of the dual-band Fabry-Perot interferometer is possible in both spectral transmission bands.

22. A process in accordance with claim 4, wherein checking of the dual-band Fabry-Perot interferometer is cyclically integrated at predetermined time intervals in the process for operating the dual-band Fabry-Perot interferometer.

23. A process in accordance with claim 22, wherein the change from the process of operating the dual-band Fabry-Perot interferometer into the process of checking the dual-band Fabry-Perot interferometer is initiated by a monitoring of a signal-to-noise ratios of the measured signals of the dual-band Fabry-Perot interferometer.

24. A process in accordance with claim 1, further comprising detecting and monitoring, with the gas concentration-measuring unit, the gas concentration of laughing gas, carbon dioxide, inhalation anesthetics and alcohols in the breathing gas of a person and/or breathing circuit of an anesthesia apparatus.

25. A process in accordance with claim 1, further comprising detecting and monitoring, with the gas concentration-measuring unit, the gas concentration of alcohols in the breathing gas of a person in the determination of the fitness to drive in road traffic or in alcohol concentration measurement for determining the fitness to work in business with respect to work activities that may be hazardous.

26. A device for gas concentration measurement, the device comprising:
a dual-band Fabry-Perot interferometer;
a first infrared radiation source for providing radiation of a first wavelength range from 4 μm to 6 μm;
a second infrared radiation source for providing a second wavelength range from 8 μm to 12 μm;

an actuating means for changing a direction of tuning of the dual-band Fabry-Perot interferometer; and a switching means for mutually switching the infrared radiation sources on and off at a time of a change in a spectral transmission band of the dual-band Fabry-Perot interferometer.

27. A device in accordance with claim 26, further comprising a means for modulating a control voltage.

28. A device in accordance with claim 26, further comprising a means for modulating the radiation sources.

29. A device for gas concentration measurement, the device comprising:

a dual-band Fabry-Perot interferometer;

a first infrared radiation source providing radiation of a first wavelength range from 4 μm to 6 μm;

a second infrared radiation source providing radiation of a second wavelength range from 8 μm to 12 μm;

an actuating means for changing a direction of tuning of the dual-band Fabry-Perot interferometer; and a switching means for mutually switching the infrared radiation sources on and off at a time of a change in the direction of tuning of the dual-band Fabry-Perot interferometer.

30. A device in accordance with claim 29, further comprising a means for modulating a control voltage.

31. A device in accordance with claim 29, further comprising a means for modulating the radiation sources.

* * * * *